US008545871B2

(12) United States Patent
Arthur et al.

(10) Patent No.: US 8,545,871 B2
(45) Date of Patent: Oct. 1, 2013

(54) FIBROUS TISSUE SEALANT AND METHOD OF USING SAME

(75) Inventors: Samuel David Arthur, Wilmington, DE (US); Tao Huang, Downingtown, PA (US); William Gerald Dimaio, Jr., Boothwyn, PA (US); George K. Kodokian, Kennett Square, PA (US)

(73) Assignee: Actamax Surgical Materials LLC, Berkeley, CA (US)

( * ) Notice: Subject to any disclaimer, the term of this patent is extended or adjusted under 35 U.S.C. 154(b) by 49 days.

(21) Appl. No.: 13/129,658

(22) PCT Filed: Aug. 31, 2009

(86) PCT No.: PCT/US2009/055487
§ 371 (c)(1),
(2), (4) Date: May 17, 2011

(87) PCT Pub. No.: WO2010/059280
PCT Pub. Date: May 27, 2010

(65) Prior Publication Data
US 2011/0250257 A1    Oct. 13, 2011

Related U.S. Application Data

(60) Provisional application No. 61/115,968, filed on Nov. 19, 2008.

(51) Int. Cl.
*A61F 13/00* (2006.01)
(52) U.S. Cl.
USPC .......................................................... 424/443

(58) Field of Classification Search
None
See application file for complete search history.

(56) References Cited

U.S. PATENT DOCUMENTS

| | | | |
|---|---|---|---|
| 6,753,454 B1 * | 6/2004 | Mello et al. ..................... | 602/41 |
| 2004/0005350 A1 | 1/2004 | Looney et al. | |
| 2006/0134185 A1 | 6/2006 | Odermatt et al. | |
| 2008/0187591 A1 | 8/2008 | Rhee et al. | |
| 2010/0272804 A1 * | 10/2010 | Lu .................................. | 424/484 |

FOREIGN PATENT DOCUMENTS

| | | |
|---|---|---|
| WO | WO2004028404 | 4/2004 |
| WO | WO2004028547 | 4/2004 |

\* cited by examiner

*Primary Examiner* — Paul Dickinson
(74) *Attorney, Agent, or Firm* — McCarter & English

(57) ABSTRACT

Disclosed herein is a fibrous tissue sealant in the form of an anhydrous fibrous sheet comprising a first component which is a fibrous polymer containing electrophilic or nucleophilic groups and a second component capable of crosslinking the first component when the sheet is exposed to an aqueous medium, thereby forming a crosslinked hydrogel that is adhesive to biological tissue. The fibrous tissue sealant may be useful as a general tissue adhesive for medical and veterinary applications such as wound closure, supplementing or replacing sutures or staples in internal surgical procedures, tissue repair, and to prevent post-surgical adhesions. The fibrous tissue sealant may be particularly suitable for use as a hemostatic sealant to stanch bleeding from surgical or traumatic wounds.

26 Claims, 2 Drawing Sheets

FIBROUS TISSUE SEALANT AND METHOD OF USING SAME

CROSS-REFERENCE TO RELATED APPLICATIONS

This application is a national stage application filed under 35 USC Section 371 of PCT/US2009/055487, filed Aug. 31, 2009, which claims the benefit of U.S. Provisional Application Serial No. 61/115,968, filed Nov. 19, 2008, both of which are incorporated herein, in entirety, by reference.

FIELD OF THE INVENTION

The invention relates to the field of medical adhesives. More specifically, the invention relates to a fibrous tissue sealant in the form of an anhydrous fibrous sheet comprising two or more crosslinkable components that react to form a crosslinked hydrogel that is adhesive to biological tissue when the sheet is exposed to an aqueous medium.

BACKGROUND OF THE INVENTION

Tissue adhesives have many potential medical applications, including wound closure, supplementing or replacing sutures or staples in internal surgical procedures, adhesion of synthetic onlays or inlays to the cornea, drug delivery devices, anti-adhesion barriers to prevent post-surgical adhesions, and as a hemostatic sealant. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, the fibrin-based adhesives do not bond covalently to the underlying tissue.

Several types of hydrogel tissue adhesives have been developed which have improved adhesive and cohesive properties and are nontoxic. These hydrogels are generally formed by reacting a component having nucleophilic groups with a component having electrophilic groups, which are capable of reacting with the nucleophilic groups of the first component to form a crosslinked network via covalent bonding. However, these hydrogels typically swell or dissolve away too quickly, or lack sufficient adhesion or mechanical strength, thereby decreasing their effectiveness as surgical adhesives.

Kodokian et al. (copending and commonly owned U.S. Patent Application Publication No. 2006/0078536) describe hydrogel tissue adhesives formed by reacting an oxidized polysaccharide with a water-dispersible, multi-arm polyether amine. These adhesives provide improved adhesion and cohesion properties, crosslink readily at body temperature, maintain dimensional stability initially, do not degrade rapidly, and are nontoxic to cells and non-inflammatory to tissue.

It is known that hydrogel tissue adhesives may be formed by mixing two aqueous solutions, each of which contains one of the crosslinkable components. The two solutions can be premixed using a mixing device before application to the desired site or can be applied separately and allowed to mix at the site of application. Additionally, the use of dried hydrogels and dried hydrogel precursors has been described (see for example, Rhee et al. U.S. Pat. No. 5,874,500, Sawhney et al., U.S. Pat. No. 6,703,047, and Odermatt et al., U.S. Patent Application Publication No. 2006/0134185). However, for some applications, for example a hemostatic sealant, it may be advantageous to have the tissue adhesive in a fibrous form which would be more effective in absorbing blood to help control bleeding and thereby having an easier application.

SUMMARY OF THE INVENTION

An anhydrous fibrous sheet comprising a first component of fibrous polymer, said polymer containing electrophilic groups or nucleophilic groups, and a second component capable of crosslinking the first component when said sheet is exposed to an aqueous medium in contact with biological tissue to form a crosslinked hydrogel that is adhesive to the biological tissue; wherein the second component is a fibrous polymer having a backbone structure the same as or different from the fibrous polymer of the first component and containing electrophilic groups if the first component contains nucleophilic groups or containing nucleophilic groups if the first component contains electrophilic groups; or the second component is a coating on the fibrous polymer of the first component, wherein said coating contains electrophilic groups if the first component contains nucleophilic groups or nucleophilic groups if the first component contains electrophilic groups; or the second component is a dry powder dispersed and entrapped within interstices of the fibrous polymer of the first component, wherein said powder contains electrophilic groups if the first component contains nucleophilic groups or nucleophilic groups if the first component contains electrophilic groups is provided.

Also provided is a method for preparing a crosslinked hydrogel useful for applying a fibrous coating to an anatomical site on tissue of a living organism, the method comprising the steps of a) applying to an anatomical site an anhydrous fibrous sheet of the invention and b) contacting the first component and the second component of the anhydrous fibrous sheet with an aqueous medium and allowing the first component and the second component to crosslink on the anatomical site to form a hydrogel that is adhesive to the tissue of the anatomical site.

Further provided is a method to obtain an adhesive hydrogel useful to stanch bleeding from a surgical or traumatic wound in tissue of a living organism, the method comprising the steps of a) applying to the wound an anhydrous fibrous sheet of the invention and b) allowing the sheet to hydrate by absorbing blood, whereby the first component and the second component crosslink to form a hydrogel that is adhesive to the tissue.

Additionally provided is a method for obtaining an adhesive hydrogel useful for applying a coating to an anatomical site on tissue of a living organism, the method comprising the steps of a) applying to the site the first component of an anhydrous fibrous sheet of the invention, b) applying to the site an aqueous solution or dispersion comprising the second component of an anhydrous fibrous sheet of the invention; and c) allowing the first component and the second component to crosslink on the site, to form a hydrogel that is adhesive to the tissue.

DETAILED DESCRIPTION

Figure 1:
FIG. 1 is a scanning electron micrograph (SEM) of the dextran aldehyde/dextran fibrous polymer described in Example 1.

As used above and throughout the description of the invention, the following terms, unless otherwise indicated, shall be defined as follows:

The term "anhydrous fibrous sheet", as used herein, refers to a nonwoven fiber in the form of a sheet or mat which is substantially water free.

The term "fibrous polymer", as used herein, refers to a natural, synthetic, or semi-synthetic polymer which is in the form of a fiber having an aspect ratio (ratio of length to diameter) of at least 1,000.

The term "crosslink" refers to a bond or chain of atoms attached between and linking two different polymer chains.

The term "crosslink density" is herein defined as the reciprocal of the average number of chain atoms between crosslink connection sites.

The term "oxidized polysaccharide" refers to a polysaccharide which has been reacted with an oxidizing agent to introduce aldehyde groups into the molecule.

The terms "equivalent weight per acetoacetate group", "equivalent weight per amine group", and "equivalent weight per aldehyde group" refer to the molecular weight of the compound divided by the number of acetoacetate, amine or aldehyde groups, respectively, in the molecule.

The term "water-dispersible polymer having nucleophilic groups" refers to a natural, synthetic, or semi-synthetic polymer containing a number "n" of nucleophilic groups (i.e., electron donating groups), such as primary amine groups, and which is water soluble or able to be dispersed in water to form a colloidal suspension capable of reacting with a second reactant containing a number "m" of electrophilic groups in an aqueous solution or dispersion to form a crosslinked hydrogel, where m plus n is greater than or equal to 5. In certain cases, a given functional group may have the properties of either electrophilicity or nucleophilicity depending upon the reaction conditions. Therefore, additionally as defined herein, water-dispersible polymers having electrophilic groups include natural, synthetic, or semi-synthetic polymers containing "m" acetoacetate groups which when treated with aqueous base to form the nucleophilic conjugate base of acetoacetate are capable of reacting with electrophilic groups, such as aldehydes.

The term "water-dispersible polymer having electrophilic groups" refers to a natural, synthetic, or semi-synthetic polymer containing a number "m" of electrophilic groups (i.e., electron accepting groups) such as aldehyde, acetoacetate, N-hydroxysuccinimidyl ester, or isocyanate, and which is water soluble or able to be dispersed in water to form a colloidal suspension capable of reacting with a second reactant containing "n" nucleophilic groups in an aqueous solution or dispersion to form a crosslinked hydrogel, where n plus m is greater than or equal to 5. Additionally as defined herein, water-dispersible polymers having electrophilic groups include natural, synthetic, or semi-synthetic polymers containing "m" carboxylic acid groups which can be activated, for example using a water-soluble carbodiimide, to react with nucleophilic groups. It can be appreciated by one skilled in the art, that not all possible nucleophiles will form a usefully stable crosslink in combination with all possible electrophiles. For instance, it is well known that a thiol will not form a particularly stable bond with an aldehyde or an acetoacetate under the conditions of hydrogel formation detailed herein. However, a thiol will form a reasonably stable thioester bond upon reaction with an N-hydroxysuccinimidyl ester under these conditions.

The term "semi-synthetic polymer" refers to a naturally occurring polymer that has been chemically modified, as for example to introduce reactive groups into the molecule.

The term "water-dispersible polymer" refers to a natural, synthetic, or semi-synthetic polymer which is water soluble or able to be dispersed in water to form a colloidal dispersion capable of reacting with a second reactant in aqueous solution or dispersion.

The term "water-dispersible, multi-arm polyether amine" refers to a branched polyether having at least three arms (i.e., branches), wherein at least three of the arms are terminated by at least one primary amine group, which is water soluble or able to be dispersed in water to form a colloidal dispersion capable of reacting with a second reactant in aqueous solution or dispersion.

The term "polyether" refers to a polymer having the repeat unit [—O—R]—, wherein R is a hydrocarbylene group having 2 to 5 carbon atoms. The polyether may also be a random or block copolymer comprising different repeat units which contain different R groups.

The term "hydrocarbylene group" refers to a divalent group formed by removing two hydrogen atoms, one from each of two different carbon atoms, from a hydrocarbon.

The term "branched polyether" refers to a polyether having one or more branch points ("arms"), including star, dendritic, comb, and hyperbranched polyethers.

The term "dendritic polyether" refers to a highly branched polyether having a tree-like structure.

The term "comb polyether" refers to a polyether having a main chain with multiple trifunctional branch points from each of which a linear arm emanates.

The term "star polyether" refers to polyether having a central branch point, which may be a single atom or a chemical group, from which linear arms emanate.

The term "hyperbranched polyether" refers to a highly branched polyether having fewer branches and less regular branching than a dendritic polyether.

The term "% by weight", also referred to herein as "wt %" refers to the weight percent relative to the total weight of the solution or dispersion, unless otherwise specified.

The term "anatomical site" refers to any external or internal part of the body of humans or animals.

The term "tissue" refers to any biological tissue, both living and dead, in humans or animals.

The term "hydrogel" refers to a water-swellable polymeric matrix, consisting of a three-dimensional network of macromolecules held together by covalent or non-covalent crosslinks, that can absorb a substantial amount of water to form an elastic gel.

The term "polyol" refers to a chemical compound having three or more OH groups.

The term "primary amine" refers to a neutral amino group having two free hydrogens. The amino group may be bound to a primary, secondary or tertiary carbon.

The term "secondary amine" refers to a neutral amino group having one free hydrogen. The amino group may be bound to a primary, secondary or tertiary carbon.

The term "PEG" as used herein, refers to poly(ethylene glycol).

The term "SEC" as used herein refers to size exclusion chromatography.

The term "DMAc" as used herein refers to N,N-dimethylacetamide.

The term "VAc" as used herein, refers to vinyl acetate.

The term "EW" as used herein refers to equivalent weight.

The term "MW" as used herein refers to molecular weight.

The term "$M_w$" as used herein refers to the weight-average molecular weight.

The term "$M_n$" as used herein refers to the number-average molecular weight.

The term "$M_z$" as used herein refers to the z-average molecular weight.

The term "NVF" as used herein refers to N-vinylformamide.

The term "medical application" refers to medical applications as related to humans and animals.

The meaning of abbreviations used is as follows: "min" means minute(s), "h" means hour(s), "sec" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "mol %" means mole percent, "Vol" means volume, "v/v" means volume per volume, "Da" means Daltons, "kDa" means kiloDaltons, the designation "10K" means that a polymer molecule possesses a number-average molecular weight of 10 kiloDaltons, "M" means molarity, "MWCO" means molecular weight cut-off, "kPa" means kilopascals, "$^1$H NMR" means proton nuclear magnetic resonance spectroscopy, "ppm" means parts per million, "PBS" means phosphate-buffered saline.

The present invention provides a fibrous tissue sealant in the form of an anhydrous fibrous sheet comprising a first component which is a fibrous polymer containing electrophilic or nucleophilic groups and a second component capable of crosslinking the first component when the sheet is exposed to an aqueous medium, thereby forming a crosslinked hydrogel that is adhesive to biological tissue. The fibrous tissue sealant may be useful as a general tissue adhesive for medical and veterinary applications including, but not limited to, wound closure, supplementing or replacing sutures or staples in internal surgical procedures such as intestinal anastomosis and vascular anastomosis, tissue repair, and to prevent post-surgical adhesions. The fibrous tissue sealant may be particularly suitable for use as a hemostatic sealant to stanch bleeding from surgical or traumatic wounds.

First Component

The first component is a fibrous polymer containing electrophilic groups or nucleophilic groups. Suitable polymers are water-dispersible polymers which can be made into fibrous polymer form. The water-dispersible polymers may have electrophilic groups, such as aldehyde, acetoacetate, or succinimidyl ester; or nucleophilic groups, such as primary amine ($NH_2$), secondary amine (NHR), carboxyhydrazide ($CONHNH_2$), acetoacetate, or thiol (SH) groups. One skilled in the art will recognize that the acetoacetate group can behave as both an electrophile, when its carbonyl groups are reacted with nucleophiles, or as a nucleophile, under basic conditions in which its methylene is deprotonated to form a stabilized carbanion capable of reacting with electrophiles. The water-dispersible polymer having electrophilic groups or the water-dispersible polymer having nucleophilic groups may be a naturally occurring polymer, such as a polysaccharide, or protein; a synthetic polymer, such as polyvinyl alcohol; a synthetic copolymer, such as poly(vinyl alcohol-co-vinyl amine); or a semi-synthetic polymer (i.e., a naturally occurring polymer that has been chemically modified), such as an oxidized polysaccharide. The synthetic polymers may be linear or branched. The water-dispersible polymers may be derivatized to introduce the desired reactive groups using methods known in the art.

Nonlimiting examples of suitable water-dispersible polymers having electrophilic groups include: oxidized polysaccharides having aldehyde groups, poly(vinyl alcohol) or poly(vinyl alcohol) copolymers derivatized with acetoacetate groups, and polysaccharides derivatized with acetoacetate groups. Nonlimiting examples of suitable water-dispersible polymers having nucleophilic groups include: poly(vinyl alcohol) or poly(vinyl alcohol) copolymers having primary amine groups, secondary amine groups, thiol groups, acetoacetate groups, or carboxyhydrazide groups, and polysaccharides having primary amine groups, secondary amine groups, thiol groups, acetoacetate groups, or carboxyhydrazide groups. Examples of these water-dispersible polymers are described below. A variety of other water-dispersible polymers having electrophilic or nucleophilic groups are known in the art and could be used to prepare the fibrous polymer disclosed herein, for example see Rhee et al. in U.S. Pat. No. 5,874,500 (in particular column 6, line 22 to column 9, line 6). It should be recognized that these other water-dispersible polymers are within the scope of the invention.

Water-Dispersible Polymers Having Electrophilic Groups (i) Oxidized Polysaccharides Polysaccharides useful in the present invention include, but are not limited to, dextran, starch, agar, cellulose, hydroxyethylcellulose, pullulan, inulin, and hyaluronic acid. These polysaccharides are available commercially from sources such as Sigma Chemical Co. (St Louis, Mo.). Suitable polysaccharides have a weight-average molecular weight from about 1,000 to about 1,000,000 Daltons, and more particularly from about 3,000 to about 250,000 Daltons.

The polysaccharide is oxidized to introduce aldehyde groups using any suitable oxidizing agent, including but not limited to, periodates, hypochlorites, ozone; peroxides, hydroperoxides, persulfates, and percarbonates. For example, the polysaccharide may be oxidized by reaction with sodium periodate as described by Mo et al. (*J. Biomater. Sci. Polymer Edn.* 11:341-351, 2000). The polysaccharide may be reacted with different amounts of periodate to give polysaccharides with different degrees of oxidation and therefore, different amounts of aldehyde groups, as described in detail in the Reagent Preparation section of the Examples below. Additionally, the oxidized polysaccharide may be prepared using the method described by Cohen et al. (copending and commonly owned Patent Application No. PCT/US08/05013, WO 2008/133847). That method of making an oxidized polysaccharide comprises a combination of precipitation and separation steps to purify the oxidized polysaccharide formed by oxidation of the polysaccharide with periodate and provides an oxidized polysaccharide with very low levels of iodine-containing species. The aldehyde content of the oxidized polysaccharide may be determined using methods known in the art. For example, the dialdehyde content of the oxidized polysaccharide may be determined using the method described by Hofreiter et al. (*Anal Chem.* 27:1930-1931, 1955), as described in detail in the Reagent Preparation section of the Examples below. In that method, the amount of alkali consumed per mole of dialdehyde in the oxidized polysaccharide, under specific reaction conditions is determined by a pH titration. Additionally, the dialdehyde content of the oxidized polysaccharide may be determined using nuclear magnetic resonance (NMR) spectroscopy. In one embodiment, the equivalent weight per aldehyde group of the oxidized polysaccharide is from about 90 to about 1500 Daltons. In another embodiment, the oxidized polysaccharide is oxidized dextran, also referred to herein as dextran aldehyde.

(ii) Poly(vinyl alcohol) or Poly(vinyl alcohol) Copolymers Derivatized with Acetoacetate Groups Poly(vinyl alcohols) having different weight-average molecular weights and varying degrees of hydrolysis are available commercially from companies such as Sigma-Aldrich (St. Louis, Mo.). Poly(vinyl alcohols) suitable for use in the invention have a weight-average molecular weight of from about 20,000 Daltons to about 100,000 Daltons, more particularly from about 30,000 Daltons to about 50,000 Daltons. Useful poly(vinyl alcohols) have a degree of hydrolysis of from about 70% to about 100% —OH groups; the remainder of the groups are acetates. Additionally, the degree of hydrolysis is from about 80% to about 100%, more specifically from about 95% to about 99%.

Additionally, copolymers of poly(vinyl alcohol), comprising poly(vinyl alcohol) units and comonomer units, may be used. Suitable comonomer units for the poly(vinyl alcohol) copolymers include, but are not limited to, ethylene, methyl acrylate, methyl methacrylate, acrylic acid, itaconic acid, maleic acid, fumaric acid, methyl vinyl ether, propylene, 1-butene, and mixtures thereof. Preferably, the copolymer comprises between about 1 mole percent and about 25 mole percent of the comonomer relative to the vinyl alcohol units.

The poly(vinyl alcohols) and the poly(vinyl alcohol) copolymers can be derivatized with acetoacetate groups by reaction with diketene, as described by Arthur in U.S. Patent Application Publication No. 2006/0079599 (in particular, paragraphs 112-113 and Examples 1-3). Alternative methods of synthesis, such as ester exchange with t-butyl acetoacetate, may also be used. Preferably, the acetoacetate derivatives have an equivalent weight per acetoacetate group of about 100 Daltons to about 2,000 Daltons.

(iii) Polysaccharides Derivatized with Acetoacetate Groups

The polysaccharides described above can also be derivatized with acetoacetate groups by reaction with diketene. For example, the preparation of dextran acetoacetate by reaction of dextran with diketene is described in detail in the Reagent Preparation section of the Example below.

Water-Dispersible Polymers Having Nucleophilic Groups
Poly(vinyl alcohol) or Poly(vinyl alcohol) Copolymers Having Primary Amine Groups Poly(vinyl alcohol) and the poly(vinyl alcohol) copolymers described above may also be derivatized with primary amine groups using methods known in the art, such as those described by Goldmann (U.S. Patent Application Publication No. 2005/0002893). Additionally, a copolymer of poly(vinyl alcohol) and vinyl amine, which can be prepared as described in the Reagent Preparation section of the Examples below, can be used as a water-dispersible polymer having nucleophilic groups.

Polysaccharides Having Primary Amine Groups

Polysaccharides containing primary amine groups can be prepared by chemical derivatization of a polysaccharide described above using methods known in the art. For example, a polysaccharide can be oxidized to produce an oxidized polysaccharide containing aldehyde groups, as described above. Then, the oxidized polysaccharide can be reacted with a diamine, such as hexamethylene diamine, ethylene diamine, propylene diamine, and the like, to form Schiff base linkages. Optionally, the Schiff base linkages may be treated with a reducing agent such as sodium borohydride to form stable carbon-nitrogen bonds. Polysaccharides containing primary amine groups may also be prepared by reacting a polysaccharide with cyanogen bromide, followed by reaction with a diamine. Additionally, polysaccharides containing primary amine groups can be prepared by the methods described by Kirakossian et al. (U.S. Pat. No. 7,179,660, Example A). The amine substitution level of the derivatized polysaccharide may be determined using proton NMR.

Preparation of the Fibrous Polymer of Component 1

The fibrous polymer comprises at least one water-dispersible polymer having electrophilic groups or nucleophilic groups, as described above. The water-dispersible polymer(s) can be spun into a fibrous polymer that comprises the first component of the anhydrous fibrous sheet disclosed herein using solution spinning methods known in the art, such as electrospinning, electro-blown spinning, or high speed rotary sprayer spinning.

Electrospinning is a well known method for spinning fiber-forming polymers into fibers (see for example, Chu et al., U.S. Pat. No. 7,172,765). Generally, a spinning solution containing a fiber-forming polymer is introduced through a nozzle into an electric field, which is formed by applying a voltage between the nozzle and a grounded target. The spinning solution exits the nozzle in the form of droplets that are attenuated into fibers by the electric field. The fibers are collected on the grounded target.

Electro-blown spinning, described by Kim et al., (U.S. Patent Application Publication No. 2005/0067732), is similar to electrospinning, but utilizes the combination of an electric field and gas flow to form fibers. Specifically, a concentric airflow is provided around the outside of the nozzle to attenuate, collimate and direct the fibers to the target. The spinning solution exits the nozzle in the form of droplets that are attenuated into fibers by the air stream and the electric field.

In high speed rotary sprayer spinning, described by Marshall et al. (U.S. Patent Application Publication No. 2008/0029617), a spinning solution containing a fiber-forming polymer is supplied to a rotary sprayer having a rotating conical nozzle, which has a concave inner surface and a forward surface discharge edge. The spinning solution flows out of the rotary sprayer along the concave inner surface so as to distribute the spinning solution toward the forward surface of the discharge edge of the nozzle, thereby forming separate fibrous streams from the spinning solution while the solvent evaporates to produce polymeric fibers in either the absence or presence of an electric field.

In one embodiment, the fibrous polymer is prepared using electro-blown spinning, as described in the Examples herein. Briefly, at least one water-dispersible polymer having electrophilic or nucleophilic groups is dissolved in a suitable solvent to prepare a spinning solution. A mixture of water-dispersible polymers having electrophilic groups or a mixture of water-dispersible polymers having nucleophilic groups may be used. The solvent may be any solvent which is capable of dissolving the water-dispersible polymer and providing a fluid capable of being electro-blown spun. Suitable solvents include, but are not limited to, water, N,N-dimethylformamide (DMF), tetrahydrofuran (THF), N,N-dimethyl acetamide, methylene chloride, dioxane, ethanol, chloroform, and mixtures thereof. In one embodiment, the solvent is water. The concentration of the water-dispersible polymer in the spinning solution is about 1% to about 80%, in more specifically about 10% to about 60% by weight relative to the total weight of the solution. The optimum concentration to be used can be readily determined by one skilled in the art using routine experimentation. Typically, the spinning solution has a viscosity of about 50 mPa·s (millipascal-seconds) to about 2,000 mPa·s. An inert polymer, such as an unmodified polysaccharide or polyether, having a high molecular weight (e.g., 100,000 Da) may be added to the spinning solution if the molecular weight of the water-dispersible polymer having electrophilic groups or nucleophilic groups is too low to provide a viscosity sufficient for spinning.

The spinning solution may optionally contain a salt which creates an excess charge effect to facilitate the electro-blown spinning process. Suitable salts include, but are not limited to, sodium chloride, potassium chloride, magnesium chloride, calcium chloride, potassium dihydrogen phosphate, potassium monohydrogen phosphate, sodium bicarbonate, and mixtures thereof.

The spinning solution may further comprise various additives depending on the intended application. The amount of the additive used depends on the particular application and may be readily determined by one skilled in the art using routine experimentation. For example, the spinning solution may comprise at least one additive selected from the group consisting of pH modifiers, viscosity modifiers, colorants, surfactants, pharmaceutical drugs and therapeutic agents.

The spinning solution may optionally include at least one pH modifier to adjust the pH of the solution. Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The spinning solution may optionally include at least one thickener. The thickener may be selected from among known viscosity modifiers, including, but not limited to, polysaccharides and derivatives thereof, such as dextran, starch or hydroxyethyl cellulose.

The spinning solution may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The spinning solution may also optionally include at least one colorant to enhance the visibility of the solution and the resulting fibrous polymer. Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No. 5, D&C Violet No.2; and natural colorants such as beetroot red, canthaxanthin, chlorophyll, eosin, saffron, and carmine.

The spinning solution may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the spinning solution may optionally include at least one pharmaceutical drug or therapeutic agent. Suitable drugs and therapeutic agents are well known in the art (for example see the United States Pharmacopeia (USP), *Physician's Desk Reference* (Thomson Publishing), *The Merck Manual of Diagnosis and Therapy* 18th ed., Mark H. Beers and Robert Berkow (eds.), Merck Publishing Group, 2006; or, in the case of animals, *The Merck Veterinary Manual,* 9th ed., Kahn, C. A. (ed.), Merck Publishing Group, 2005). Nonlimiting examples include anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; anti-coagulants such as heparin; peptides; antibacterial agents; antiviral agents; antifungal agents; anti-cancer agents; healing promoters; adhesion promoters; vaccines; and thrombogenic agents such as thrombin, fibrinogen, heparin binding molecules and/or peptide sequences such as HIP peptide, factor VII, factor XIIIa, molecules to stabilize clot formation via endogenous or exogenous factor XIIIa, such as molecules containing glutamine and/or lysine residues.

The spinning solution may be spun into a fibrous polymer using an electro-blown spinning apparatus, containing a metal tube, also referred to as a spinneret, which is charged relative to a grounded target. The voltage applied between the metal tube and the grounded target is typically in the range of about 30 to about 100 kilovolts (kV), in more specifically about 70 to about 100 kV. The spinning solution is pumped through a metal tube with an inside diameter typically of 0.01 to 0.03 inches (0.254 to 0.762 mm) at a feed rate appropriate to the solution viscosity and wt % solids content, typically about 0.1 to about 2.0 milliliters per minute. A concentric airflow is provided around the outside of the metal tube to attenuate, collimate and direct the fibers to the target. The spinning solution exits the metal tube in the form of droplets that are attenuated into fibers by the air stream and the electric field. The fiber may be deposited onto a support fabric, such as a REEMAY® spunbound polyester fabric, positioned over the target to receive the spun fiber. The spinning unit may be contained in a spinning chamber, such as a polymethacrylate or polycarbonate box, in which the temperature and humidity are controlled. Typically, the humidity in the spinning chamber is maintained at about 10% to about 50% at a temperature of about 25° C. to about 50° C.

Second Component

The second component of the anhydrous fibrous sheet disclosed herein comprises at least one water-dispersible polymer having electrophilic groups or nucleophilic groups, which is capable of crosslinking the first component when the sheet is exposed to an aqueous medium, thereby forming a crosslinked hydrogel that is adhesive to biological tissue. Specifically, if the first component is the fibrous form of a water-dispersible polymer having electrophilic groups, the second component is a water-dispersible polymer having nucleophilic groups that are capable of reacting with the electrophilic groups of the first component to form a crosslinked hydrogel. Conversely, if the first component is the fibrous form of a water-dispersible polymer having nucleophilic groups, the second component is a water-dispersible polymer having electrophilic groups that are capable of reacting with the nucleophilic groups of the first component to form a crosslinked hydrogel. The second component may be a mixture of different water-dispersible polymers having electrophilic groups or nucleophilic groups capable of crosslinking the first component. The backbone structure of the second component can be the same as or different from that of the fibrous polymer of the first component. The second component may have electrophilic groups including, but not limited to, aldehyde, acetoacetate, succinimidyl, and isocyanate. The second component may have nucleophilic groups including, but not limited to, primary amine, secondary amine, carboxyhydrazide, acetoacetate, and thiol.

Suitable water-dispersible polymers having electrophilic groups or nucleophilic groups for use as the second component include those described above for the first component. Additional suitable water-dispersible polymers having electrophilic groups for use as the second component include, but are not limited to, linear or branched polyethers derivatized with acetoacetate groups, linear or branched polyethers derivatized with aldehyde groups, linear or branched polyethers derivatized with isocyanate groups, and linear or branched polyethers derivatized with N-hydroxysuccinimidyl ester groups. Additional examples of suitable water-dispersible polymers having nucleophilic groups for use as the second component include: linear or branched polyethers derivatized with primary amine or secondary amine groups, linear or branched polyethers derivatized with thiol groups, and linear or branched polyethers derivatized with carboxyhydrazide groups. Some examples of these water-dispersible polymers are described below.

Linear or Branched Polyethers Derivatized with Primary Amine Groups

The linear or branched polyethers are water-dispersible polymers having the repeat unit [—O—R]—, wherein R is an hydrocarbylene group having 2 to 5 carbon atoms. The term "hydrocarbylene group" refers to a divalent group formed by removing two hydrogen atoms, one from each of two different carbon atoms, from a hydrocarbon. Useful linear or branched polyethers have a number-average molecular weight of about 300 Daltons to about 100,000 Daltons, more particularly from about 500 Daltons to about 20,000 Daltons. Suitable examples of linear or branched polyethers include, but are not limited to, linear or branched poly(ethylene oxide), linear or branched poly(propylene oxide), linear or branched copolymers of poly(ethylene oxide) and poly(propylene oxide), linear or branched poly(1,3-trimethylene oxide), linear or branched poly(1,4-tetramethylene oxide), star poly(ethylene oxide), comb poly(ethylene oxide), star poly(propylene oxide), comb poly(propylene oxide), and mixtures thereof. Many linear polyethers are available commercially from companies such as Sigma-Aldrich (St Louis, Mo.). Many branched polyethers are available from companies such as Nektar Transforming Therapeutics (Huntsville, Ala.), SunBio, Inc. (Anyang City, South Korea), NOF Corp. (Tokyo, Japan), or JenKem Technology (USA, Allen, Tex.). For example, the water-dispersible polymer having nucleophilic groups may be a linear or multi-arm branched polyether amine. The linear and branched polyethers described above may be derivatized with primary amine end groups using methods known in the art (see for example, *Poly(Ethylene Glycol) Chemistry: Biotechnical and Biomedical Applications*, J. Milton Harris, Ed., Plenum Press, NY, 1992, Chapter 22). Preferably, the amine derivatives have an equivalent weight per amine group of about 100 Daltons to about 2,000 Daltons. Examples of multi-arm polyether amines include, but are not limited to, dendritic, comb, and star polyethers wherein at least three of the arms are terminated by a primary amine group. The multi-arm polyether amines have a number-average molecular weight of about 450 to about 100,000 Daltons. Suitable examples of water-dispersible, multi-arm polyether amines include, but are not limited to, amino-terminated star, dendritic, or comb polyethylene oxides; amino-terminated star, dendritic or comb polypropylene oxides; amino-terminated star, dendritic or comb polyethylene oxide-polypropylene oxide copolymers; and polyoxyalkylene triamines, sold under the trade name Jeffamine® triamines, by Huntsman LLC. (Houston, Tex.). Examples of star polyethylene oxide amines, include, but are not limited to, various multi-arm polyethylene glycol amines and star polyethylene glycols having 3, 4, 6, or 8 arms terminated with primary amines (referred to herein as 3, 4, 6 or 8-arm star PEG amines, respectively). The 8-arm star PEG amine is available from Nektar Transforming Therapeutics. Examples of suitable Jeffamine® triamines include, but are not limited to, Jeffamine® T-403 (CAS No. 39423-51-3), Jeffamine® T-3000 (CAS No. 64852-22-8), and Jeffamine® T-5000 (CAS No. 64852-22-8). In one embodiment, the water-dispersible multi-arm polyether amine is an 8-arm polyethylene glycol having eight arms terminated by a primary amine group and having a number-average molecular weight of about 10,000 Daltons, which can be prepared as described in the Reagent Preparation section of the Examples below. In another embodiment, the water-dispersible multi-arm polyether amine is a 4-arm polyethylene glycol having four arms terminated by a primary amine group and having a number-average molecular weight of about 2,000 Daltons, which can be prepared as described in the Reagent Preparation section of the Examples below.

These multi-arm polyether amines are either available commercially, as noted above, or may be prepared using methods known in the art. For example, multi-arm polyethylene glycols, wherein at least three of the arms are terminated by a primary amine group, may be prepared by putting amine ends on multi-arm polyethylene glycols (e.g., 3, 4, 6, and 8-arm star polyethylene glycols, available from Nektar Transforming Therapeutics, SunBio Corp., and NOF Corp.) using the method described by Buckmann et al. (Makromol. Chem. 182:1379-1384, 1981). In that method, the multi-arm polyethylene glycol is reacted with thionyl bromide to convert the hydroxyl groups to bromines, which are then converted to amines by reaction with ammonia at 100° C. The method is broadly applicable to the preparation of other multi-arm polyether amines. Additionally, multi-arm polyether amines may be prepared from multi-arm polyols using the method described by Chenault (copending and commonly owned U.S. Patent Application Publication No. 2007/0249870). In that method, the multi-arm polyether is reacted with thionyl chloride to convert the hydroxyl groups to chlorine groups, which are then converted to amines by reaction with aqueous or anhydrous ammonia. Other methods that may be used for preparing multi-arm polyether amines are described by Merrill et al. in U.S. Pat. No. 5,830,986, and by Chang et al. in WO 97/30103.

The multi-arm amine may also be a multi-arm branched end amine, as described by Arthur (copending and commonly owned Patent Application No. PCT/US07/24393, WO 2008/066787). The multi-arm branched end amines are branched polymers having two or three primary amine groups at the end of each of the polymer arms. The multiplicity of functional groups increases the statistical probability of reaction at a given chain end and allows more efficient incorporation of the molecules into a polymer network. The starting materials used to prepare the multi-arm branched end amines are branched polymers such as multi-arm polyether polyols including, but not limited to, comb and star polyether polyols. The branched end amines can be prepared by attaching multiple amine groups to the end of the polymer arms using methods well known in the art. For example, a multi-arm branched end amine having two primary amine functional groups on the end of each of the polymer arms can prepared by reacting the starting material, as listed above, with thionyl chloride in a suitable solvent such as toluene to give the chloride derivative, which is subsequently reacted with tris (2-aminoethyl)amine to give the multi-arm branched end reactant having two amine groups at the end of the polymer arms. In one embodiment, the water-dispersible multi-arm amine is an 8-arm polyethylene glycol hexadecaamine having a number-average molecular weight of about 40,000 Daltons, which can be prepared as described in the Reagent Preparation section of the Examples below.

It should be recognized that the multi-arm polyether amines are generally a somewhat heterogeneous mixture having a distribution of arm lengths and in some cases, a distribution of species with different numbers of arms. When a multi-arm amine has a distribution of species having different numbers of arms, it can be referred to based on the average number of arms in the distribution. For example, in one embodiment the multi-arm amine is an 8-arm star PEG amine, which comprises a mixture of multi-arm star PEG amines, some having less than and some having more than 8 arms; however, the multi-arm star PEG amines in the mixture have an average of 8 arms. Therefore, the terms "8-arm", "6-arm", "4-arm" and "3-arm" as used herein to refer to multi-arm amines, should be construed as referring to a heterogeneous mixture having a distribution of arm lengths and in some cases, a distribution of species with different numbers of arms, in which case the number of arms recited refers to the average number of arms in the mixture.

Additionally, other multi-arm amines, such as amino-terminated dendritic polyamidoamines, sold under the trade name Starburst® Dendrimers (available from Sigma-Aldrich, St Louis, Mo.), may be used as water-dispersible polymers having nucleophilic groups.

Linear or Branched Polyethers Derivatized with Secondary Amine Groups

Many of the principles described above for the preparation of polymers functionalized with primary amines also pertain to the preparation of polymers bearing secondary amine groups. For instance the method of Chenault (U.S. Patent Application Publication No. 2007/0249870) referenced above can be adapted by using a mono-substituted amine (e.g., methylamine) rather than ammonia as a reactant.

Linear or Branched Polyethers Derivatized with Thiol Groups

The water-dispersible polymer having nucleophilic groups may also be a linear or multi-arm polyether thiol. The linear and branched polyethers described above may be derivatized with thiol groups using methods known in the art involving conversion of the polyether hydroxy ends to toluenesulfonate ends and subsequent reaction with sodium hydrosulfide to give thiol ends (see for example, Harris et al, *ACS Polymer Preprints* 32:154, (1991)). Preferably, the thiol derivatives have an equivalent weight per thiol group of about 100 Daltons to about 2,000 Daltons and have a number-average molecular weight of about 300 to about 100,000 Daltons. Examples of multi-arm polyether thiols include, but are not limited to, dendritic, comb, and star polyethers wherein at least three of the arms are terminated by a thiol group.

Linear or Branched Polyethers Derivatized with Carboxyhydrazide Groups

The water-dispersible polymer having nucleophilic groups may also be a linear or multi-arm polyether carboxyhydrazide. The linear and branched polyethers described above may be derivatized with carboxyhydrazide groups using methods known in the art involving conversion of the polyether hydroxy ends to ethyl acetourethane ends via reaction with ethyl isocyanatoacetate followed by reaction with hydrazine to give carboxyhydrazide ends (see for example, *Poly (Ethylene Glycol): Chemistry and Biological Applications*, J. Milton Harris et al, Eds., ACS Symposium Series 680, NY, 1997, Chapter 21). Preferably, the carboxyhydrazide derivatives have an equivalent weight per carboxyhydrazide group of about 100 Daltons to about 2,000 Daltons and have a number-average molecular weight of about 300 to about 100,000 Daltons. Examples of multi-arm polyether carboxyhydrazides include, but are not limited to, dendritic, comb, and star polyethers wherein at least three of the arms are terminated by a carboxyhydrazide group.

Linear or Branched Polyethers Derivatized with Acetoacetate Groups

The water-dispersible polymer having electrophilic groups may be a linear or multi-arm polyether acetoacetate. The linear and branched polyethers may be derivatized with acetoacetate groups by reaction with diketene, as described by Arthur in U.S. Patent Application Publication No. 2006/0079599. Preferably, the acetoacetate derivatives have an equivalent weight per acetoacetate group of about 100 Daltons to about 2,000 Daltons and have a number-average molecular weight of about 300 to about 100,000 Daltons. Examples of multi-arm polyether acetoacetates include, but are not limited to, dendritic, comb, and star polyethers wherein at least three of the arms are terminated by an acetoacetate group.

Linear or Branched Polyethers Derivatized with Aldehyde Groups

The water-dispersible polymer having electrophilic groups may be a linear or multi-arm polyether aldehyde. The linear and branched polyethers described above may be derivatized with aldehyde groups using methods known in the art. For example, the primary hydroxy-ended linear and branched polyethers may be converted to toluenesulfonate ends, reacted with sodium hydrosulfide to give thiol ends and subsequently reacted with 3-chloropropionaldehyde diethyl acetal followed by hydrolysis to give thiol-linked aldehyde ends (Harris et al., *ACS Polymer Preprints* 32:154 (1991)). Another polyether aldehyde synthesis is described by Harris (*Poly(Ethylene Glycol) Chemistry: Biotechnical and Biomedical Applications*, J. Milton Harris, Ed., Plenum Press, NY, 1992, Chapter 22). Alternatively, a polyether functionalized with aldehyde groups can be prepared by reacting primary hydroxy-ended linear and branched polyethers with thionyl chloride to give a polyether having chloride ends, reacting the chloride-ended polyether with 1-thioglycerol in the presence of a base to yield a thiomethylethyleneglycol-functionalized polyether, which is subsequently oxidized with an oxidizing agent such as periodate to give a thiomethylaldehyde polyether, as described in detail in the Reagent Preparation section of the Examples herein. Additionally, polyethylene glycols derivatized with aldehyde groups are available from commercial sources, such as Nektar Transforming Therapeutics. Preferably, the aldehyde derivatives have an equivalent weight per aldehyde group of about 100 Daltons to about 2,000 Daltons and have a number-average molecular weight of about 300 to about 100,000 Daltons. Examples of multi-arm polyether aldehydes include, but are not limited to, dendritic, comb, and star polyethers wherein at least three of the arms are terminated by an aldehyde group.

Linear or Branched Polyethers Derivatized with N-Hydroxysuccinimidyl Ester Groups The water-dispersible polymer having electrophilic groups may also be a linear or multi-arm polyether N-hydroxysuccinimidyl ester. The linear and branched polyethers described above may be derivatized with N-hydroxysuccinimidyl ester groups using methods known in the art involving conversion of the polyether hydroxy ends to carboxylic acids by carboxymethylation followed by reaction with a combination of N-hydroxysuccinimide and 1-(3-dimethylaminopropyl)-3-ethylcarbodiimide HCl (EDC) (see for example, *Poly(Ethylene Glycol) Chemistry: Biotechnical and Biomedical Applications*, J. Milton Harris, Ed., Plenum Press, NY, 1992, Chapter 21), Preferably, the N-hydroxysuccinimidyl ester derivatives have an equivalent weight per N-hydroxysuccinimidyl ester group of about 100 Daltons to about 2,000 Daltons and have a number-average molecular weight of about 300 to about 100,000 Daltons. The multi-arm polyether N-hydroxysuccinimidyl esters include, but are not limited to, dendritic, comb, and star polyethers wherein at least three of the arms are terminated by a N-hydroxysuccinimidyl ester group.

Linear or Branched Polyethers Derivatized with Isocyanate Groups

The water-dispersible polymer having electrophilic groups may also be a linear or multi-arm polyether having isocyanate groups. The linear or branched polyethers described above may be derivatized with isocyanate groups using methods known in the art (e.g., Zavatsky, U.S. Patent Application Publication No. 2008/0039548). For example, a linear PEG diisocyanate can be made by converting the PEG bis(carboxymethyl ether) to the corresponding bis(acyl chloride) which is converted to the bis(acyl azide) and thermally rearranged to the diisocyanate, as described in detail in the Reagent Preparation section of the Examples below.

Combinations of Components

Nonlimiting examples of useful combinations of water-dispersible polymers for the first and second components are given below. Other combinations of water-dispersible polymers having electrophilic groups and water-dispersible polymers having nucleophilic groups that are known in the art are also contemplated to be within the scope of the invention. If the first component is an oxidized polysaccharide containing aldehyde groups, (e.g., oxidized dextran); a poly(vinyl alcohol) or poly(vinyl alcohol) copolymer derivatized with acetoacetate groups; or a polysaccharide derivatized with acetoacetate groups, the second component may be a linear or branched polyether derivatized with primary amine groups or carboxyhydrazide groups, a polysaccharide having amine groups, a poly(vinyl alcohol) or a poly(vinyl alcohol) copolymer having amine groups. If the first component is a poly(vinyl alcohol) or poly(vinyl alcohol) copolymer derivatized with acetoacetate groups; or a polysaccharide derivatized with acetoacetate groups, the second component may also be a linear or branched polyether derivatized with secondary amine groups, a polysaccharide derivatized with secondary amine groups, or a poly(vinyl alcohol) or a poly(vinyl alcohol) copolymer derivatized with secondary amine groups. If the first component is a poly(vinyl alcohol) or poly(vinyl alcohol) copolymer having primary amine groups or carboxyhydrazide groups; or a polysaccharide having primary amine groups or carboxyhydrazide groups, the second component may be an oxidized polysaccharide containing aldehyde groups (e.g. oxidized dextran); a poly(vinyl alcohol) or poly(vinyl alcohol) copolymer derivatized with acetoacetate groups; a polysaccharide derivatized with acetoacetate groups; or a linear or branched polyether derivatized with acetoacetate groups, aldehyde groups, isocyanate groups, or N-hydroxysuccinimidyl groups. If the first component is a poly(vinyl alcohol) or poly(vinyl alcohol) copolymer having secondary amine groups; or a polysaccharide having secondary amine groups, the second component may be a poly(vinyl alcohol) or poly(vinyl alcohol) copolymer derivatized with acetoacetate groups; a polysaccharide derivatized with acetoacetate groups; or a linear or branched polyether derivatized with acetoacetate groups, isocyanate groups, or N-hydroxysuccinimidyl groups. If the first component is a poly(vinyl alcohol) or poly(vinyl alcohol) copolymer having thiol groups or a polysaccharide having thiol groups, the second component may be a linear or branched polyether derivatized with N-hydroxysuccinimidyl groups.

In yet another embodiment, the first component is a fibrous polymer comprising an oxidized polysaccharide having aldehyde groups such as oxidized dextran and the second component comprises a multi-arm polyether amine, such as an 8-arm or 4-arm PEG amine, or an 8-arm PEG hexadecaamine.

In yet another embodiment, the first component is a fibrous polymer comprising a poly(vinyl alcohol-co-vinyl amine) and the second component comprises a 4-arm PEG thiomethylaldehyde or a linear PEG bis(thiomethylaldehyde).

In another embodiment, the first component is a fibrous polymer comprising oxidized dextran and the second component comprises dextran acetoacetate. In this embodiment, the two polymers are combined in a single solution and are electro-blown spun to afford fibers containing both components which are unreactive until activated. The anhydrous fibrous sheet comprising the first and second components is treated with an aqueous base solution to effect dissolution and crosslinking of the hydrogel via condensation of the nucleophilic conjugate base of acetoacetate with the electrophilic dextran aldehyde groups.

In yet another embodiment, the first component is a fibrous polymer comprising oxidized dextran and the second component comprises poly(vinyl alcohol-co-vinyl amine).

In another embodiment, the first component is a fibrous polymer comprising a poly(vinyl alcohol) or poly(vinyl alcohol) copolymer having primary amine groups, such as poly(vinyl alcohol-co-vinyl amine), and the second component comprises a linear or branched polyether derivatized with isocyanate groups, such as a linear PEG diisocyanate.

The second component may be present in the anhydrous fibrous sheet in various forms. For example, in one embodiment the second component is present as a second fibrous polymer, prepared using the methods described above for the first component, and spun as a second layer on top of the first fibrous polymer layer. In another embodiment, the second component is a fibrous polymer that is cospun from a second spinning solution through a separate spinning orifice, simultaneously with the first component to form a fibrous sheet with intermingled fibers of both components.

In another embodiment, the second component is a coating on the fibrous polymer of the first component. In this embodiment, the second component is dissolved in a suitable solvent that dissolves the second component, but does not dissolve the fibrous polymer comprising the first component, The fibrous polymer is coated with the solution of the second component using methods known in the art, for example, applying the solution to the fibrous polymer using a delivery device such as a pipette, dip coating, spray coating, and the like. The coated fibrous polymer is dried to remove the solvent, thereby forming the anhydrous fibrous sheet.

In another embodiment, the second component is a dry powder that is dispersed and entrapped within the interstices of the web of fibrous polymer of the first component.

For use in medical applications it is preferred that the anhydrous fibrous sheet disclosed herein be sterilized to prevent infection. Suitable sterilization methods include, but are not limited to, gamma irradiation, electron beam irradiation, and ultraviolet irradiation.

Various additives may be incorporated into the anhydrous fibrous sheet. Any of the additives described above may be used. The additive may be coated onto the anhydrous fibrous sheet using coating methods well known in the art. Additionally, a dry powder additive may be dispersed and entrapped within the interstices of the web of fibrous polymer of the first component or the second component, if present as a fibrous polymer. Alternatively, the additive may be covalently coupled to the anhydrous fibrous sheet through the electrophilic or nucleophilic groups present on the first and/or second component.

The anhydrous fibrous sheet may also comprise a non-stick coating on at least one surface to allow convenient application of the fibrous sheet to tissue, so as to prevent, for example, the surgeon's glove from becoming adherent to the sealant patch. The coating may comprise a silicone, such as polydimethylsiloxane, polyethylene glycols, fatty acids, and polysaccharides such as dextran.

The anhydrous fibrous sheet may also comprise a non-biodegradable, peelable backing to aid in the application of the fibrous sheet to tissue. The non-biodegradable backing may be a solid sheet or film comprising one or more layers comprised of polymers such as polytetrafluoroethylene or copolymers thereof, polyethylene, polyacrylate, polyester, polyurethane, nylon, polydimethysiloxane, and the like. These films may be constructed as is typically done for release sheets and/or for barrier-layer films for packaging applications, including metalized polymer films. The non-biodegradable backing is removed after application of the anhydrous fibrous sheet to the tissue site.

The anhydrous fibrous sheet may also comprise a biodegradable, backing to aid in the application of the fibrous sheet to tissue. The biodegradable backing may be a sheet or film comprising a biodegradable polymer such as for example, a polymer comprising one or more monomers selected from the group consisting of a glycolide, lactide, lactic acid, dioxanone, caprolactone, trimethylene carbonate, ethylene glycol, propylene glycol, and lysine. Additionally, various biodegradable, adhesion prevention films, such as oxidized regenerated cellulose (for example Interceed® absorbable adhesion barrier, available form Ethicon, Inc., Raleigh, N.C.) sodium hyaluronate/carboxymethylcellulose (for example Seprafilm® adhesion barrier available from Genzyme, Cambridge, Mass.), gelatin, collagen, polyvinyl alcohol, and chitosan film may be used as the biodegradable backing.

Medical Applications of the Fibrous Tissue Sealant

The fibrous tissue sealant, disclosed herein, may be useful as a general tissue adhesive for medical and veterinary applications including, but not limited to, wound closure, supplementing or replacing sutures or staples in internal surgical procedures such as intestinal anastomosis and vascular anastomosis, tissue repair, and to prevent post-surgical adhesions. The fibrous tissue sealant may be particularly suitable for use as a hemostat to stanch bleeding from surgical or traumatic wounds.

In one embodiment, the fibrous tissue sealant is used to apply a coating to an anatomical site on tissue of a living organism. The coating may act as a sealant or adhesive, or as an antiadhesive coating to prevent post-surgical adhesions. To apply the coating, the anhydrous fibrous sheet disclosed herein is applied to the site and the first and second components are hydrated and allowed to crosslink at the site to form a hydrogel that is adhesive to tissue. The fibrous sheet may be applied to the site in various ways, such as using gloved fingers, sterile forceps, or other sterile applicator. The fibrous sheet may be hydrated by body fluids present at the site or by the addition an aqueous medium, such as an aqueous buffer solution.

In another embodiment, the fibrous tissue sealant is used to stanch bleeding from a surgical or traumatic wound in tissue of a living organism. In this embodiment, the anhydrous fibrous sheet disclosed herein is applied to the site of the wound and allowed to hydrate by absorbing blood, whereby the first component and the second component crosslink to form a hydrogel that is adhesive to tissue.

In another embodiment, a coating is applied to an anatomical site on tissue of a living organism by applying the fibrous polymer of the first component to the site, applying the second component in the form of an aqueous solution or dispersion to the site, and allowing the first and the second component to crosslink on the site, thereby forming a hydrogel that is adhesive to the tissue. The aqueous solution or dispersion comprises from about 5% to about 70% by weight of the second component relative to the total weight of the aqueous solution or dispersion. The aqueous solution or dispersion may be applied to the site in a variety of ways, for example, applying with a syringe or spray device.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

A reference to "Aldrich" or a reference to "Sigma" means the said chemical or ingredient was obtained from Sigma-Aldrich, St. Louis, Mo.

Reagent Preparation

Preparation of Dextran Aldehyde (D10-50)

Dextran aldehyde having an average molecular weight of about 10 kDa and a degree of oxidation of about 50%, referred to herein as D10-50, is made by oxidizing dextran in aqueous solution with sodium metaperiodate. An oxidized dextran with about 50% oxidation conversion (i.e., about half of the glucose rings in the dextran polymer were oxidized to dialdehydes) is prepared from dextran having a weight-average molecular weight of 8,500 to 11,500 Daltons (Sigma) by the method described by Cohen et al. (copending and commonly owned Patent Application No. PCT/US08/05013). A typical procedure is described here.

A 20-L reactor equipped with a mechanical stirrer, addition funnel, internal temperature probe, and nitrogen purge is charged with 1000 g of the dextran and 9.00 L of de-ionized water. The mixture is stirred at ambient temperature to dissolve the dextran and then cooled to 10 to 15° C. To the cooled dextran solution is added over a period of an hour, while keeping the reaction temperature below 25° C., a solution of 1000 g of sodium periodate dissolved in 9.00 L of de-ionized water. Once all the sodium periodate solution has been added, the mixture is stirred at 20 to 25° C. for 4 more hours. The reaction mixture is then cooled to 0° C. and filtered to clarify. Calcium chloride (500 g) is added to the filtrate, and the mixture is stirred at ambient temperature for 30 min and then filtered. Potassium iodide (400 g) is added to the filtrate, and the mixture is stirred at ambient temperature for 30 min. A 3-L portion of the resulting red solution is added to 9.0 L of acetone over a period of 10 to 15 min with vigorous stirring by a mechanical stirrer during the addition. After a few more minutes of stirring, the agglomerated product is separated from the supernatant liquid. The remaining red solution obtained by addition of potassium iodide to the second filtrate is treated in the same manner as above. The combined agglomerated product is broken up into pieces, combined with 2 L of methanol in a large stainless steel blender, and blended until the solid becomes granular. The granular solid is recovered by filtration and dried under vacuum with a nitrogen purge. The granular solid is then hammer milled into a fine powder. A 20-L reactor is charged with 10.8 L of de-ionized water and 7.2 L of methanol, and the mixture is cooled to 0° C. The granular solid formed by the previous step is added to the reactor and the slurry is stirred vigorously for one hour. Stirring is discontinued, and the solid is allowed to settle to the bottom of the reactor. The supernatant liquid is decanted by vacuum, 15 L of methanol is added to the reactor, and the slurry is stirred for 30 to 45 min while cooling to 0° C. The slurry is then filtered in portions, and the recovered solids are washed with methanol, combined, and dried under vacuum with a nitrogen purge to give about 600 g of the oxidized dextran, which is referred to herein as D10-50.

The degree of oxidation of the product is determined by proton NMR to be about 50% (equivalent weight per aldehyde group=146). In the NMR method, the integrals for two ranges of peaks are determined, specifically, —$O_2$CHx- at about 6.2 parts per million (ppm) to about 4.15 ppm (minus the HOD peak) and —OCHx- at about 4.15 ppm to about 2.8 ppm (minus any methanol peak if present). The calculation of oxidation level is based on the calculated ratio (R) for these areas, specifically, R=(OCH)/(O₂CH).

Preparation of Dextran Aldehyde (D100-6)

Dextran aldehyde having an average molecular weight of about 100 kDa and a degree of oxidation of about 6%, referred to herein as D100-6, is made by oxidizing dextran in aqueous solution with sodium metaperiodate. An oxidized dextran with about 5-10% oxidation (i.e., about 5-10% of the glucose rings in the dextran polymer were oxidized to dialdehydes) is prepared from dextran having a weight-average molecular weight of 100,000 to 200,000 Daltons (Sigma). A solution of 2.0 g sodium periodate in 15 mL of deionized water is added all at once with stirring to a solution of 22 g dextran D100 (Sigma D4876; Mw=100-200 kDa) in 150 mL of deionized water and the solution is stirred for 4 hours at room temperature. After 4 hours, 1 mL of ethylene glycol is added to the reaction to destroy any remaining periodate and the solution is stirred for 15 min more. Then 1 g of calcium chloride dihydrate is added and the solution is magnetically stirred in an ice bath for 1 hour and then suction-filtered through a coarse frit to remove calcium iodate hexahydrate. The clear filtrate is then combined with 0.5 g of potassium iodide with magnetic stirring, resulting in a red solution which is stirred at room temperature for 30 min. The solution is poured into 1000 mL of acetone and swirled briefly to produce a suspension of swollen liquid dextran aldehyde which coats out on the walls of the flask. After standing for 30 min, the acetone is poured off and the polymer is stirred with a spatula with 200 mL of methanol, which hardens the polymer. The methanol is decanted off after 10 min and the polymer is blended in a Waring blendor with 500 mL methanol for 5 min. The resulting suspension is suction-filtered and dried overnight under a nitrogen blanket to yield 19.8 g of dextran aldehyde D100-6. The degree of oxidation of the product is determined by proton NMR to be about 6% (equivalent weight per aldehyde group=1335).

Preparation of Eight-Arm PEG 40K Hexadecaamine (P8-40-2)

Eight-arm PEG 40K ($M_n$=40 kDa) hexadecaamine, having two amino groups on the end of each arm, is synthesized via the reaction of 8-arm PEG 40K chloride with tris(2-aminoethyl)amine, i.e.,

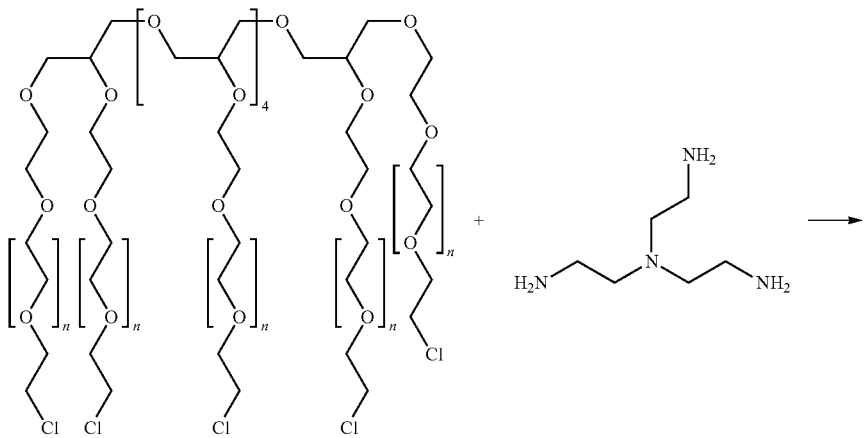

8-Arm PEG 40K Chloride

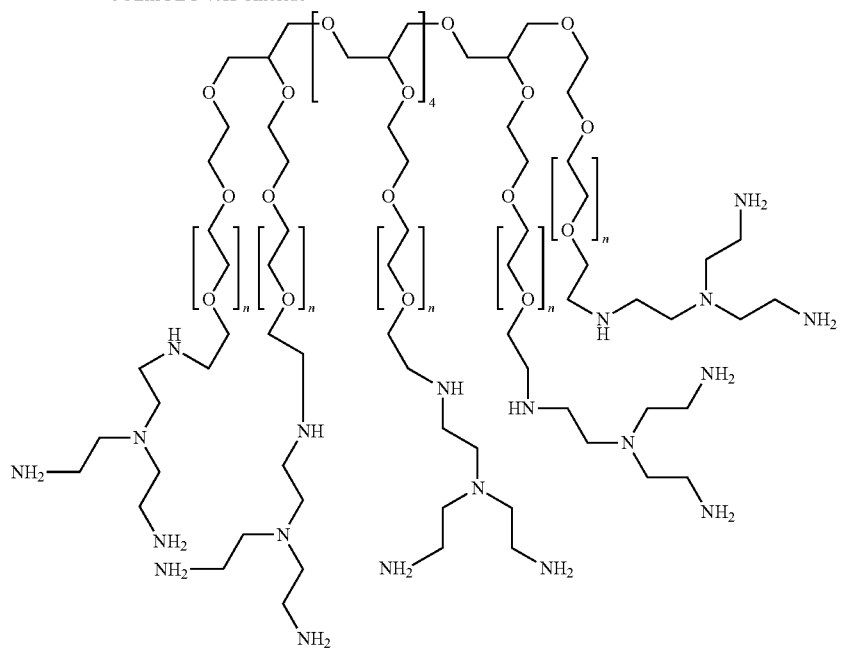

8-Arm PEG 40K Chloride

The 8-arm PEG 40K chloride is made by reaction of thionyl chloride with the 8-arm PEG 40K octaalcohol. A typical procedure is described here.

A solution of 100 g (20 mmol OH) of 8-arm PEG 40K ($M_n$=40,000; NOF SunBright HGEO-40000) in 200 mL of toluene is heated to 70° C. and stirred under nitrogen as 6 mL of thionyl chloride (10 g; 80 mmol) is quickly added. The mixture is stirred at 60° C. under nitrogen for 20 hours, after which the solution is bubbled with nitrogen for 1 hour while still warm to remove thionyl chloride and then 2 mL (50 mmol) of methanol is added to scavenge remaining thionyl chloride. The resulting solution is added, with stirring, to 300 mL of hexane to initially make a gelatinous precipitate which soon becomes friable and powdery as the toluene extracts from the product. The white suspension is stirred for an hour and then suction-filtered on a glass-fritted funnel, washed once with 100 mL of hexane and suctioned-dry on the funnel under a nitrogen blanket to yield the 8-arm PEG 40K chloride.

A solution of 30.0 g (6.0 mmol Cl) of 8-arm PEG 40K chloride in 60 mL of water is rapidly stirred as 36 mL (35.3 g; 240 mmol) of tris(2-aminoethyl)amine (TCI America, Portland, Oreg.; #T1243) is added. The resulting solution is stirred in a 100° C. oil bath under nitrogen for 25 hours. Then, 0.5 mL (9 mmol) of 50% sodium hydroxide is added and the mixture is cooled and extracted with 150 mL of dichloromethane followed by 2 extractions with 100 mL portions of dichloromethane. Separation is somewhat slow but is eventually complete overnight. The combined extracts are dried with sodium sulfate, evaporated to a volume of 120 mL using rotary evaporation, and precipitated into 850 mL of diethyl ether with stirring. The ether is then stirred in an ice bath and the resulting white precipitate is suction-filtered on a glass-fritted funnel under nitrogen, washed with 100 mL of diethyl ether and suctioned dry on the funnel under nitrogen to yield the 8-arm PEG 40K hexadecaamine, referred to herein as P8-40-2.

Proton NMR results from one preparation are:

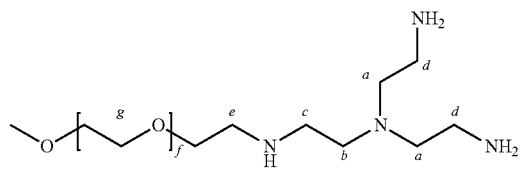

$^1$H NMR (500 MHz; CDCl$_3$): δ 2.53 ppm (t, J=6.0 Hz, a); 2.60 (t, J=6.1 Hz, b); 2.71 (t, J=6.1 Hz, c); 2.76 (t, J=5.9 Hz, d); 2.80 (t, J=5.2 Hz, e); 3.59 (t, J=5.3 Hz, f); 3.64 (s, g); 3.76 CH$_2$Cl (t, J=6.0 Hz; h; gone). Integrate groups of peaks: 2.5-2.8 ppm (a-e; 14.3H; theory 14H); 3.5-3.8 ppm (f-g, PEG backbone, 500H). There is no remaining tris(2-aminoethyl)amine by NMR.

Preparation of Eight-Arm PEG 10K Octaamine (P8-10-1)

Eight-arm PEG 10K octaamine ($M_n$=10 kDa) is synthesized using the two-step procedure described by Chenault in co-pending and commonly owned U.S. Patent Application Publication No. 2007/0249870. In the first step, the 8-arm PEG 10K chloride is made by reaction of thionyl chloride with the 8-arm PEG 10K octaalcohol. In the second step, the 8-arm PEG 10K chloride is reacted with aqueous ammonia to yield the 8-arm PEG 10K octaamine. A typical procedure is described here.

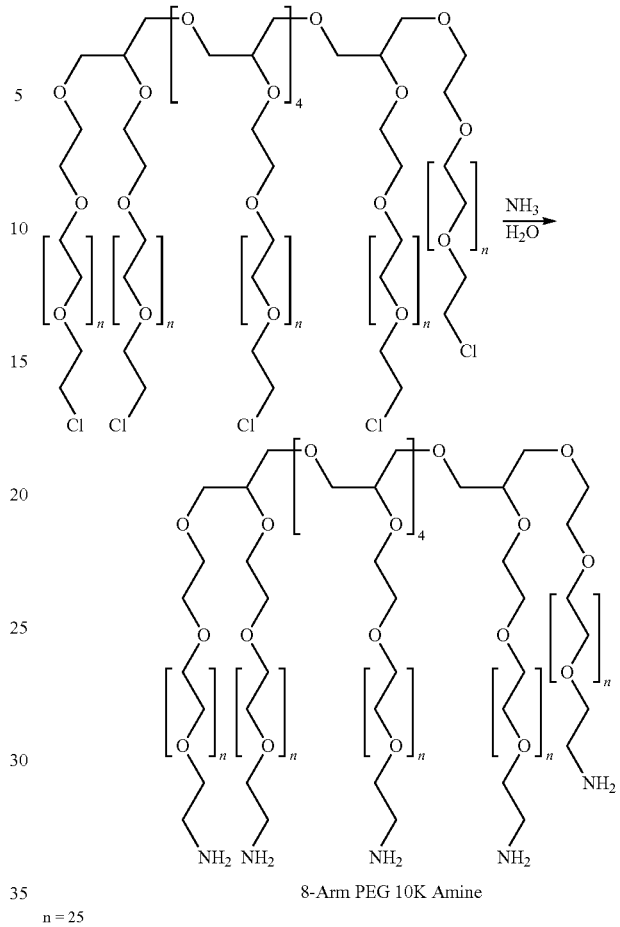

8-Arm PEG 10K Amine n = 25

The 8-arm PEG 10K octaalcohol ($M_n$=10000; NOF SunBright HGEO-10000), (100 g in a 500-mL round-bottom flask) is dried either by heating with stirring at 85° C. under vacuum (0.06 mm of mercury (8.0 Pa)) for 4 h or by azeotropic distillation with 50 g of toluene under reduced pressure (2 kPa) with a pot temperature of 60° C. The 8-arm PEG 10K octaalcohol is allowed to cool to room temperature and thionyl chloride (35 mL, 0.48 mol) is added to the flask, which is equipped with a reflux condenser, and the mixture is heated at 85° C. with stirring under a blanket of nitrogen for 24 hours. Excess thionyl chloride is removed by rotary evaporation (bath temp 40° C.). Two successive 50-mL portions of toluene are added and evaporated under reduced pressure (2 kPa, bath temperature 60° C.) to complete the removal of thionyl chloride.

$^1$H NMR (500 MHz, DMSO-d6) δ 3.71-3.69 (m, 16H), 3.67-3.65 (m, 16H), 3.50 (s, ~800H).

The 8-arm PEG 10K octachloride (100 g) is dissolved in 640 mL of concentrated aqueous ammonia (28 wt %) and heated in a pressure vessel at 60° C. for 48 hours. The solution is sparged for 1-2 hours with dry nitrogen to drive off 50 to 70 g of ammonia. The solution is then passed through a column (500 mL bed volume) of strongly basic anion exchange resin (Purolite® A-860, The Purolite Co., Bala-Cynwyd, Pa.) in the hydroxide form. The eluant is collected and three 250-mL portions of de-ionized water are passed through the column and also collected. The aqueous solutions are combined, concentrated under reduced pressure (2 kPa, bath temperature 60° C.) to about 200 g, frozen in portions and lyophilized to give the 8-arm PEG 10K octaamine, referred to herein as P8-10-1, as a colorless waxy solid.

Preparation of Four-Arm PEG 2K Tetraamine (P4-2-1)

A 4-arm PEG 2K ($M_n$=2 kDa) tetraamine is prepared using a similar procedure as described above for the 8-arm PEG 10K octaamine.

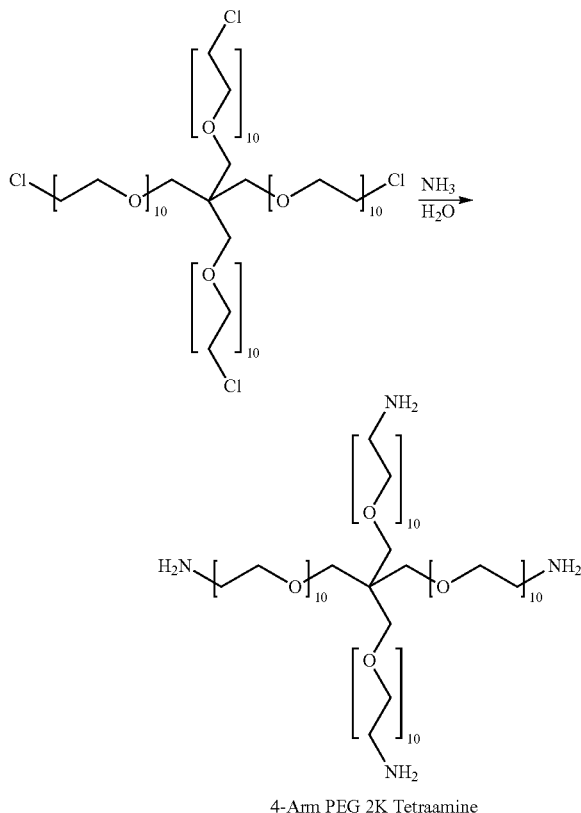

4-Arm PEG 2K Tetraamine

Four-arm PEG 2K tetraalcohol ($M_n$=2000; NOF SunBright PTE-2000), (100 g in a 500-mL round-bottom flask) is dissolved in 100 mL of dichloromethane. Thionyl chloride (88 mL, 1.2 mol) is added, and the mixture is stirred under a blanket of nitrogen at ambient temperature for 24 hours. Excess thionyl chloride and dichloromethane are removed by rotary evaporation (bath temp 40° C.). Two successive 50-mL portions of toluene are added and evaporated under reduced pressure (2 kPa, bath temperature 60° C.) to complete the removal of thionyl chloride.

Proton NMR results from one preparation are:

$^1$H NMR (500 MHz, DMSO-d6): δ 3.71-3.68 (m, 8H), 3.67-3.65 (m, 8H), 3.57-3.55 (m, 8H), 3.50 (m, ~140H), 3.47-3.45 (m, 8H), 3.31 (s, 8H).

The 4-arm PEG 2K tetrachloride (40 g) is dissolved in 600 mL of concentrated aqueous ammonia (28 wt %) and heated in a pressure vessel at 60° C. for 48 hours. The solution is cooled and sparged for 1.5 hours with dry nitrogen, and then concentrated by rotary evaporation (2 kPa, bath temperature 60° C.) to about 500 g. The solution is then passed through a column (500 mL bed volume) of strongly basic anion exchange resin (Purolite® A-860) in the hydroxide form. The eluant is collected, and two 250-mL portions of de-ionized water are passed through the column and collected. The aqueous fractions are combined and evaporated under reduced pressure (2 kPa, bath temperature 60° C.) to give the 4-arm PEG 2K tetraamine, referred to herein as P4-2-1, as a clear, pale-yellow liquid.

$^1$H NMR (500 MHz, CDCl$_3$): δ 3.65-3.51 (m, ~170H), 3.47 (m, 8H), 3.36 (s, 8H), 2.86 (t, J=5.3 Hz, 7.4H), 2.76 (t, J=5.4 Hz, 0.6H).

Preparation of Poly(vinyl alcohol-co-vinyl amine) Method A

A copolymer of vinyl alcohol and vinyl amine is made by copolymerizing vinyl acetate and N-vinylformamide followed by hydrolysis. A thiol chain transfer agent is employed to limit polymer molecular weight and provide a practical spinning solution viscosity.

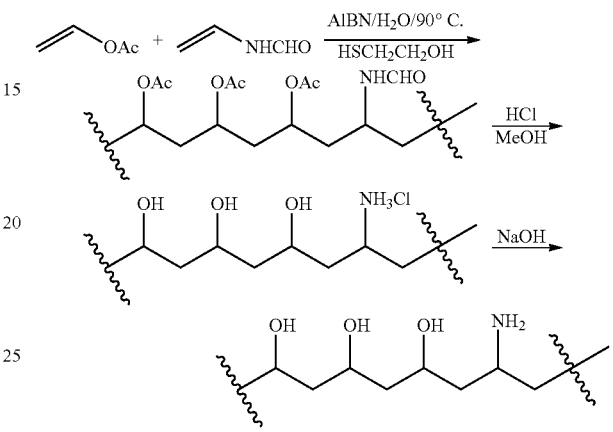

A solution of 0.1 g sodium dodecylbenzenesulfonate in 80 mL of deionized water is placed in a 250-mL, 4-neck round-bottom flask with condenser and nitrogen inlet, thermometer, 2 dropping funnels and a magnetic stirrer. The flask is swept with nitrogen and stirred in a 90° C. oil bath until the solution temperature is 90° C.; then 0.1 g of AIBN (2,2'-azobisisobutyronitrile; Aldrich 441090) initiator is added. A solution of 32 g vinyl acetate (Aldrich V1503; filtered through basic alumina to remove inhibitor), 5 g N-vinylformamide (Aldrich 447331; as received) and 0.10 mL of 2-mercaptoethanol (Aldrich M3701) is placed in a larger dropping funnel under nitrogen, and a solution of 1.0 g AIBN in 9 mL of vinyl acetate is placed in a smaller dropping funnel. Four milliliters of the thiol-containing monomer solution and 1 mL of the AIBN-containing monomer solution are then added to the flask with stirring and the polymerization proceeds at 90° C. under refluxing vinyl acetate (boiling point of 72° C.). The mixture is stirred for 20 min and another 4 mL+1 mL of the two monomer solutions, respectively, are added, after which the mixture becomes increasingly opaque white. The 4 mL+1 mL of the two monomer solutions are added every 20 min for 1 hour; then the mixture is stirred for 1 hour at 90° C. After this time, the remainder of the monomers are added at a rate of 4 mL+1 mL every 20 min. When the monomers are all added (about 4 hours), the mixture is stirred at 90° C. for 2 hours more and then the heating bath is removed. The suspension is rotary evaporated to remove monomer and water and the damp sludge is taken up in 250 mL of methanol. An aliquot is precipitated with diethyl ether and dried under high vacuum for analysis by proton NMR and size exclusion chromatography.

$^1$H NMR (500 MHz; DMSO-d6): by ratio of the 3.80-ppm N-vinylformamide methine peak to the 4.78-ppm vinyl acetate methine peak, the polymer has 11.2 mol % N-vinylformamide incorporation (hydrolyzed amine EW=390). Size exclusion chromatography (dimethylacetate) results: $M_n$=44,700; $M_w$=447,000; $M_z$=2,086,000; $M_w/M_n$=10.0; g'=0.81; α=0.59.

Ten milliliters of concentrated hydrochloric acid is added to the methanol solution of polymer and the resulting mixture is stirred at reflux for 24 hours, during which time a rubbery polymer precipitates and coagulates. Proton NMR (DMSO-d6) shows that the acetate groups are gone. Filtration and drying under nitrogen yields 18.3 g of the poly(vinyl alcohol-co-vinyl amine hydrochloride) product. The product is dissolved in 170 mL of deionized water and the resulting solution is filtered through a 5-pm membrane filter. The filtered solution is basified to pH 9.0 (measured with a pH electrode) with NaOH and the solution is desalted by dialysis against deionized water in a MEMBRA-CELL® (Viskase Companies, Inc., Willowbrooke, Ill.) 3.5K MWCO (molecular weight cut-off) dialysis membrane tube. The dialyzed poly(vinyl alcohol-co-vinyl amine) solution is then adjusted to 20 wt % by rotary evaporation to remove excess water. This polymer solution is kept protected from atmospheric carbon dioxide which would react with the amine groups to form unreactive carbamates.

Preparation of Poly(vinyl alcohol-co-vinyl amine) Method B

A poly(vinyl alcohol-co-vinyl amine) polymer is made using carbon tetrachloride as a chain transfer agent rather than mercaptoethanol as in Method A.

A monomer solution of 40.0 g vinyl acetate (Aldrich V1503; filtered through alumina to remove inhibitor) and 5.0 g N-vinylformamide (Aldrich 447331) is syringe-filtered to remove a small amount of polymer. Then, 0.10 g of carbon tetrachloride (0.12 mol % based on monomer) and 0.3 g of AIBN (2,2'-azobisisobutyronitrile; Aldrich 441090) are added to the solution.

A solution containing 0.1 g of sodium dodecylbenzenesulfonate and 0.1 g of sodium dihydrogen phosphate in 80 mL of deionized water is placed in a 250-mL, 4-neck round-bottom flask with condenser, nitrogen inlet, thermocouple well, monomer inlet line and magnetic stir bar. The flask is swept with nitrogen and stirred in a 70° C. water bath until the solution temperature reaches 65° C. Then, 0.1 g of AIBN initiator is added to the flask, followed immediately by the addition of 5 mL of monomer solution with stirring. The remainder of the monomer solution is placed in a 60-mL syringe on a syringe pump and the solution is delivered to the flask at a rate of 0.25 mL/min over 3 hours. When the monomer solution has all been added, the mixture is stirred in the 70° C. bath for 1 hour more, and then the heating bath is removed and the suspension is cooled to 22° C., resulting in the formation of a gooey mixture, which is rotary evaporated to remove vinyl acetate and water. The resulting material is taken up in 50 mL of methanol and the solution is poured into ice water with stirring to give a congealed soft rubber polymer. The polymer is worked (masticated by hand) in hot water to remove soap and monomer and then chilled in ice water, forming a stiffer polymer which can be torn apart into fibrils. The polymer is soaked in water overnight and then filtered and dried under vacuum to yield poly(vinyl acetate-co-vinyl formamide).

$^1$H NMR (500 MHz; DMSO-d6): by ratio of the 3.80-ppm NVF methine peak (1.84) to the 4.77-ppm VAc methine peak (14.45), the polymer has 11.3 mol % N-vinylformamide incorporation (hydrolyzed amine EW=390). Size exclusion chromatography (SEC) Results (DMAc): $M_n$=60,310; $M_w$=202,160; $M_z$=464,260; $M_w/M_n$=3.35; [η]=0.62; α=0.51.

The poly(vinyl acetate-co-vinyl formamide) product is stirred in a 500-mL resin kettle with 250 mL of methanol and 10 mL (0.1 mol) of concentrated hydrochloric acid at reflux for 16 hours. The mixture becomes a solution in about an hour, and a rubbery polymer begins to separate at about 6 hours. The rubbery polymer is cut up with scissors into 1-cm chunks, washed with methanol and dried under nitrogen on a funnel to yield 30.5 g of rubbery poly(vinyl alcohol-co-vinyl amine hydrochloride) polymer. This polymer is stirred with 100 mL of deionized water on a hot plate to give a solution which is then basified to pH 10 with 10 wt % NaOH. This solution is dialyzed in a MEMBRA-Cell® (Viskase Companies, Inc., Willowbrooke, Ill.) 3.5K MWCO dialysis tube in stirred deionized water for 24 hours. The water is changed twice in the first 6 hours. The top of the bucket containing the water is kept covered with aluminum foil and nitrogen is continuously bubbled through the water in the bucket to keep carbon dioxide in the air from reacting with the amino polymer. The dialyzed solution is frozen in liquid nitrogen and lyophilized to yield 12.4 g of poly(vinyl alcohol-co-vinyl amine).

It should be noted that thiol chain transfer (Method A) is preferable to carbon tetrachloride in controlling the molecular weight of the poly(vinyl acetate-co-vinyl formamide), in that the poly(vinyl alcohol-co-vinyl amine) polymers produced using thiols can be dissolved to a higher percent solids content without forming gels at a given molecular weight. Many other chain transfer agents can be used, such as methanol or isopropanol.

Preparation of Four-Arm PEG 2K Tetra(thiomethylaldehyde)

A 4-arm PEG 2K tetra(thiomethylaldehyde) is prepared by reacting 4-arm PEG 2K tetrachloride with 1-thioglycerol to give a 4-arm PEG 2K with thiomethylethyleneglycol ends. Oxidation of this intermediate with one equivalent of sodium metaperiodate per glycol group yields the 4-arm PEG 2K terminated with thiomethylaldehyde groups.

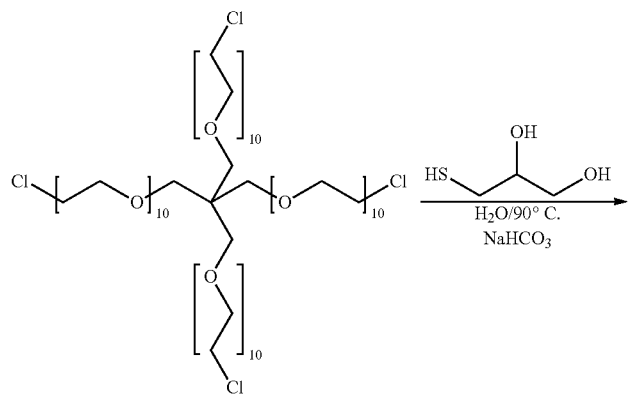

-continued

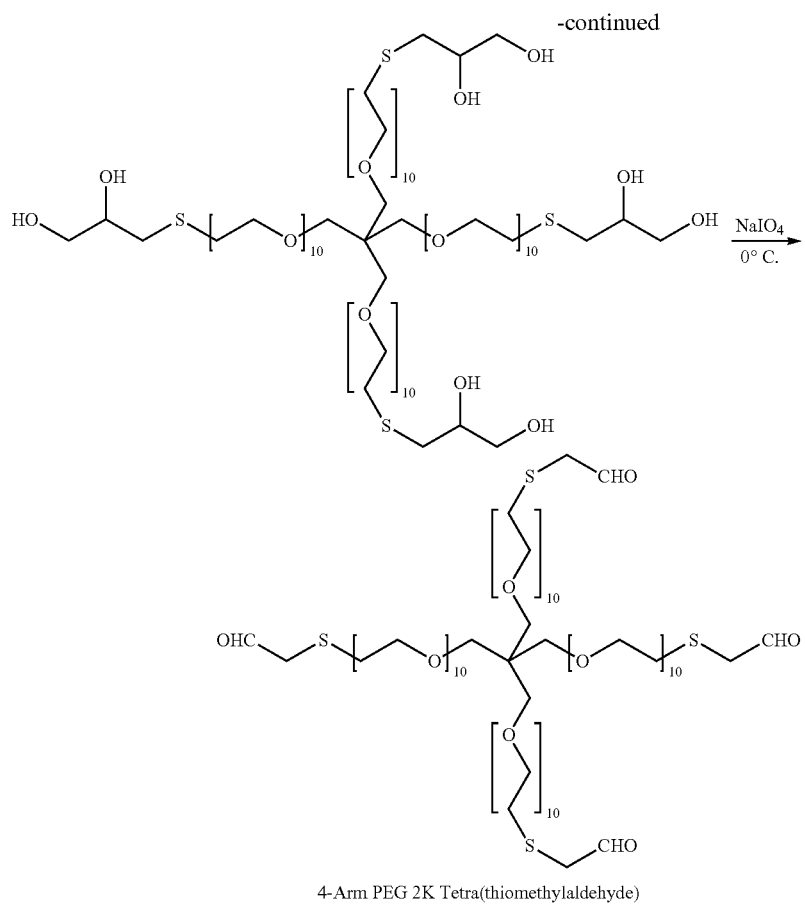

4-Arm PEG 2K Tetra(thiomethylaldehyde)

A solution of 10.0 g (20 mmol Cl) 4-arm PEG 2K tetrachloride, described above in the preparation of 4-Arm PEG 2K tetraamine (P4-2-1), 2.5 g (30 mmol) sodium bicarbonate and 3.5 g (32 mmol) 1-thioglycerol (Aldrich M1753) in 30 mL of water is stirred in a 90° C. oil bath under nitrogen for 22 hours. The solution is cooled to room temperature and extracted with three 35 mL portions of dichloromethane. The combined extracts are dried with sodium sulfate followed by magnesium sulfate, filtered, concentrated to 20-25 mL and precipitated with stirring in 500 mL of diethyl ether with chilling in ice. The product is still a liquid at 0° C., so stirring is stopped and the flask is cooled in dry ice. The ether is decanted off the white product which has solidified on the bottom of the flask. The flask is warmed to room temperature and the liquefied product is stirred with 200 mL of fresh ether and chilled again in dry Ice. The ether is decanted off and the product is taken up in dichloromethane (50 mL) and transferred to a round-bottom flask. The solvent is removed by rotary evaporation and the concentrate is held under high vacuum to yield 7.5 g of 4-arm PEG 2K tetra(thiomethylethyleneglycol) as a clear liquid.

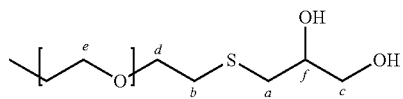

$^1$H NMR (500 mHz; CDCl$_3$): δ 2.70 ppm (ABX q of d, 2H, a); 2.76 (t, J=6.1 Hz, 2H, b); 3.41 (s, pentaerythritol core CH$_2$O, 2H); 3.54 (m, 3H, c); 3.59 (t, J=4.7 Hz, 2H, d); 3.64 (s, 46H, e); 3.75 (t, CH$_2$Cl, gone); 3.81 (m, 1H, f).

A solution of 2.0 g (3.5 mmol diol; EW approximately equal to 575; M$_n$ approximately equal to 2300) 4-arm PEG 2K tetra(thiomethylethyleneglycol) in 20 mL of deionized water is stirred in an ice bath as a solution of 0.75 g (3.5 mmol) sodium metaperiodate in 10 mL of water is added in 3-mL portions every 5 min. The mixture is allowed to stir at 0° C. for 60 min and then 5 drops of ethylene glycol are added and the solution is extracted with four 25 mL portions of dichloromethane. The combined extracts are dried with magnesium sulfate and concentrated by rotary evaporation from a warm tap water bath to about 15 mL. The concentrate is added with stirring to 150 mL of diethyl ether. The mixture is stirred for 15 min and then cooled in dry ice to freeze the product. The ether is decanted off, replaced with 100 mL of fresh ether and the mixture is warmed to room temperature and stirred for 10 min, followed by freezing and decanting again. The product is then taken up in 25 mL of dichloromethane, transferred to a 100-mL round-bottom flask, and rotary evaporated from a warm tap water bath. The concentrate is held under vacuum at 22° C. with a nitrogen bleed through a syringe needle to remove solvent, yielding 1.10 g of liquid 4-arm PEG 2K tetra(thiomethylaldehyde).

Infrared (neat): 1716 cm−1 (CHO)

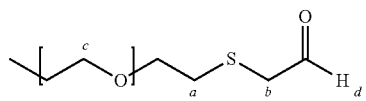

$^1$H NMR (500 MHz; CDCl$_3$): δ 2.66 ppm (t, J=6.1 Hz, 2H, a); 3.27 ppm (d, J=3.5 Hz, 2H, b); 3.64 ppm (s, 46H, c); 9.51 ppm (t, J=3.3 Hz, 0.8H d). By ratio of the SCH$_2$CHO integral (9.51 ppm) to S(=O)CH$_2$CHO integral (9.86 ppm). The product contains about 12 mol % sulfoxide aldehyde ends due to over-oxidation with excess metaperiodate. This compound is unstable with respect to self-condensation due to the acidic methylene between the aldehyde and sulfoxide and therefore is best used promptly.

Preparation of Linear PEG 600 Bis(thiomethylaldehyde)

A low molecular weight linear PEG bis(thiomethylaldehyde) is made by converting the PEG diol to the corresponding dichloride, converting the dichloride to the bis(thiomethylethyleneglycol), which is oxidized to the bis(thiomethylaldehyde).

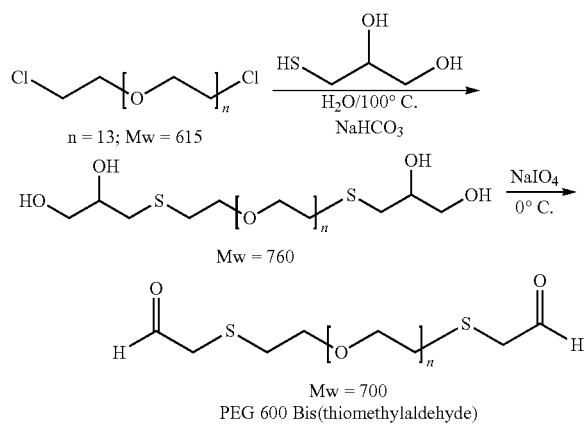

Mw = 700
PEG 600 Bis(thiomethylaldehyde)

A solution of 20 g (67 mmol OH) PEG 600 (M$_n$=600; Aldrich 202401) and 0.2 mL of N,N-dimethylacetamide in 60 mL of toluene in a 200-mL round-bottom flask is stirred in a 70° C. oil bath as 7.5 mL of thionyl chloride (12 g; 100 mmol) is added dropwise down the condenser. The solution is stirred under nitrogen at 70° C. for 20 hours. The mixture is rotary evaporated to remove about half of the toluene. The resulting concentrate is added to ether chilled in an ice bath, and then chilled in dry ice to separate a slurry which is quickly filtered cold and then added to 200 mL of hexane. The resulting solid, which is very sticky and low-melting, is taken up in dichloromethane, rotary evaporated and held under vacuum under a nitrogen stream from a needle through a septum to remove solvent. The resulting PEG 600 dichloride (10.4 g) is a brown oil.

$^1$H NMR (500 MHz; CDCl$_3$): δ 3.64 ppm (s, OCH$_2$CH$_2$O backbone; 52H); 3.76 ppm (t, J=5.9 Hz, ClCH$_2$CH$_2$O; 4H).

A solution of 9.0 g (29 mmol Cl) PEG 600 dichloride, 4.0 g (48 mmol) sodium bicarbonate and 4.3 g (40 mmol) 1-thioglycerol (Aldrich M1753) in 25 mL of water is stirred in a 100° C. oil bath under nitrogen for 16 hours. The solution is extracted with four—40 mL portions of dichloromethane. The combined extracts are dried with magnesium sulfate, filtered, concentrated to 20 mL and precipitated from 200 mL of diethyl ether chilled in an ice bath. The product is still a liquid at 0° C., so stirring is stopped and the flask is cooled in dry ice. The ether is decanted off the white product which has solidified on the bottom of the flask. The flask is warmed to room temperature and the liquefied product is stirred with 200 mL of fresh ether and chilled again in dry ice. The ether is decanted off and the product is taken up in dichloromethane (50 mL) and transferred to a round-bottom flask. The solvent is rotary evaporated off and the resulting concentrate is held under vacuum with a nitrogen purge through a syringe needle to yield 7.4 g of PEG 600 bis(thiomethylethyleneglycol).

$^1$H NMR (500 MHz; CDCl$_3$): δ 2.71 ppm (ABX q of d, 4H); 2.77 (t, J=6.1 Hz, 4H); 3.55 (m, 2H); 3.64 (s, 52H); 3.69 (t, J=6.2 Hz, ~6H); 3.75 (t, CH$_2$Cl, gone); 3.83 (m, 2H).

A solution of 6.00 of g (15.8 mmol diol; EW approximately equal to 380; M$_n$ approximately equal to 760) PEG 600 bis(thiomethylethyleneglycol) in 30 mL of deionized water is stirred in an ice bath as a solution of 3.40 g (16 mmol) sodium metaperiodate in 30 mL of water is added at a rate of 1 mL/min using a syringe pump. Following the addition, the mixture is allowed to stir at 0° C. for 60 min and then 10 drops of ethylene glycol are added and the solution is extracted with four—40 mL portions of dichloromethane. The combined extracts are dried with magnesium sulfate and concentrated by roto evaporation from a warm tap water bath to a volume of about 15 mL. The concentrate is added with stirring to 200 mL of diethyl ether. The mixture is stirred for 15 min and then cooled in dry ice to freeze the product. The ether is decanted off, replaced with 100 mL of fresh ether and the mixture is warmed to room temperature and stirred for 10 min, followed by freezing and decanting again. The product is then taken up in dichloromethane and transferred to a 100-mL round-bottom flask, rotary evaporated from a warm tap water bath, and then held under vacuum at 22° C. with a nitrogen bleed through a syringe needle to remove solvent, yielding 2.0 g of PEG 600 bis(thiomethylaldehyde) as an orange liquid.

Infrared (neat): 1716 cm-1 (CHO). This product is stable under nitrogen for months.

$^1$H NMR (500 MHz; CDCl$_3$): δ 2.66 ppm (t, J=6.2 Hz, 4H); 3.27 (d, J=3.3 Hz, 4H); 3.64 (s, 88H); 9.51 (t, J=3.3 Hz, 2H); There is <1% over-oxidized sulfoxide aldehyde present.

Preparation of Dextran Acetoacetate

Dextran acetoacetate is prepared by reacting dextran with diketene.

Dextran (55 g; Sigma D4876; M$_w$=100-200 kDa) is dried in a vacuum oven under a nitrogen stream at 100° C. and 300 mm Hg (40 kPa) for 3 hours. A 15.0-g sample of the dried dextran (unit mw=162.14; OH eq wt=54; 278 mmol OH) is combined with 160 mL of dry N,N-dimethylacetamide and 0.2 g of N,N-4-dimethylaminopyridine in a 500-mL round-bottom flask under nitrogen. The mixture is purged by bubbling with nitrogen for 5 min and then is magnetically stirred in a 100° C. oil bath to give a cream-colored suspension. To this mixture, 5 g of dry lithium chloride is added and a clear yellow solution results in about 10 min. The solution is cooled and stirred at 22° C. as 6.0 mL (6.5 g; 78 mmol) of freshly sublimated diketene (Aldrich #302058; distilled at 0.4 mm Hg (0.05 kPa) to a liquid nitrogen-cooled cold finger condenser) is added by syringe over a period of 30 sec. The internal temperature slowly rises to about 40° C. and then cools. The resulting yellow solution is stirred at 22° C. for 22 hours and then is blended into 700 mL of methanol in a Waring® blender (Waring Products, Torrington, Conn.) to afford a blob of soft, taffy-like polymer. The polymer mass is stretched out and cut into 1-cm pieces with scissors and fed to 500 mL of acetone in a blender. Blending for 15 min results in a suspension of solid particulate polymer which is suction-filtered on a coarse glass-fritted funnel and suctioned dry under a nitrogen blanket to yield 17.8 g of dextran acetoacetate as a water-soluble tan powder.

The acetoacetate content is determined by proton NMR in D$_2$O. The ratio of the acetoacetate CH$_3$ peak (2.35 ppm, 3H) with the dextran skeletal CH peaks (3.4-4.1 ppm and 4.8-5.3 ppm; 7H total per glucose unit) gives a degree of substitution=0.74; equivalent weight per acetoacetate group=303.

Preparation of Linear PEG 600 Diisocyanate

The PEG 600 diisocyanate is made by converting the PEG 600 bis(carboxymethyl ether) to the corresponding bis(acyl chloride) which is converted to the bis(acyl azide) and thermally rearranged to the diisocyanate.

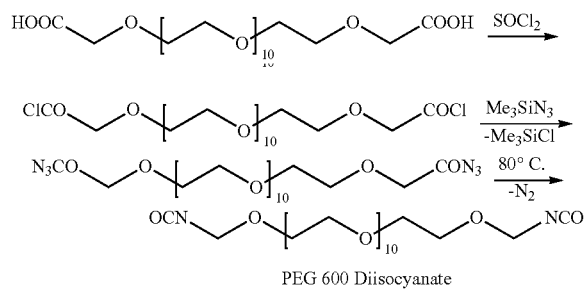

PEG 600 Diisocyanate

A solution of 15 g of PEG bis(carboxymethyl ether) (50 mmol COOH; EW=300; Aldrich 407038) and 3 drops of N,N-dimethylacetamide in 40 mL of dichloromethane is stirred at room temperature in a 100-mL round-bottom flask with a condenser as 8.1 g of thionyl chloride (5.0 mL; 68 mmol) is added down the condenser. A drying tube is placed on the condenser and the solution is stirred at reflux for 3 hours. If infra-red spectrospcopic analysis indicates the presence of some remaining COOH (1753 cm$^{-1}$), an additional 1 mL of thionyl chloride is added and the mixture is stirred at reflux for 2 hours more, at which time infra-red spectroscopic analysis should indicate completion of the reaction. The solution is rotary evaporated to remove solvent and thionyl chloride. The PEG 600 bisacyl chloride is stirred in a hot water bath under a nitrogen stream to remove traces of HCl and is taken up in 40 mL of dry toluene. Then, 10.0 mL of azidotrimethylsilane (8.7 g, 75 mmol; Aldrich 155071) is added and the solution is stirred under nitrogen and slowly heated in an oil bath to 80° C. over 45 min and then held at 80° C. for 15 min. The solution is rotary evaporated from a 70° C. water bath, then held in the bath and stirred under a nitrogen stream for 2 hours, and finally is stirred under high vacuum in the water bath for 1 hour to yield 14.5 g of PEG 600 diisocyanate as a brown liquid. PEG 600 bisacyl chloride IR (neat): 1805 cm$^{-1}$ (COCl) PEG 600 diisocyanate IR (neat): 2252 cm$^{-1}$ (NCO)

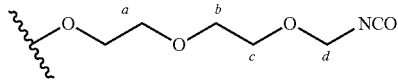

$^1$H NMR (CDCl$_3$): 3.64 ppm (s, 47H, a); 3.69 (m, 4H, b); 3.75 (m, 4H, c); 4.84 (s, 4H, d); 4.18 (s, 0.5H); 4.30 (t, 0.5H)

Example 1

Preparation of an Anhydrous Fibrous Sheet Comprising Dextran Aldehyde and Eight-Arm PEG 40K Hexadecaamine (P8-40-2)

The following Example demonstrates the preparation of an anhydrous fibrous sheet comprising a fibrous polymer containing dextran aldehyde and dextran that is impregnated with eight-arm PEG 40K hexadecaamine (P8-40-2). A solution containing dextran aldehyde and dextran was electro-blown spun into a fibrous dextran sheet, into which was added finely ground solid P8-40-2 PEG amine.

A mixture of 20 g of dextran aldehyde solution containing 25 wt % of D10-48 (M$_w$=10 kDa; oxidation level=48% of glucose rings cleaved to dialdehydes; prepared as described in Reagent Preparations) in water and 7 g of dextran 100K (M$_w$=100 kDa; Aldrich D4876) was prepared. The mixture initially gave a fluid solution but became a gel on standing at 22° C. for 30 min. The gel was stirred and warmed to 50° C. with 10 g of water to give a fluid solution which was stable over 3-4 hours; this solution contained 14 wt % D10-48 and 19 wt % dextran 100K. This solution was spun into fibers by electro-blown spinning.

The electro-blown spinning apparatus consisted of a 0.016 inch (0.41 mm) metal tube orifice in the center of a polytetrafluoroethylene (PTFE) plate charged at 100 kV relative to a grounded target, which was a rotating 8-inch (20.3 cm) diameter metal drum covered with a REEMAY® spunbonded polyester (Fiberweb Inc., London) support fabric to receive the spun fiber which accumulated to form a sheet on the drum. The solution containing dextran aldehyde (D10-48) and dextran 100K was fed to the orifice via a plastic syringe pressurized with nitrogen. The orifice was positioned pointing down toward the target drum from 24-36 cm away and a concentric airflow was provided around the outside of the orifice to collimate and direct the fibers toward the metal drum. The current across the gap between the orifice and drum was typically about 40-60 μA. Depending on the polymer solution viscosity, nitrogen pressures of 30-120 psig (207-827 kPa) were used to extrude the polymer solution from the spinning orifice at about 1 mL/min in droplets that were attenuated into fibers by the air stream and the electrostatic field. The spinning unit was contained in a clear polycarbonate box. Relative humidity in the spinning chamber was kept at about 10-20% at 25-30° C. by means of two heated nitrogen streams impinging on opposite sides of the metal drum.

The solution spun very well; the fiber plume was quite wide, indicating the polymer solution was well-charged. The fibrous polymer mat spun from this solution was about a millimeter thick, and contained 42 wt % D10-48 and 58 wt % dextran 100K. The fibers had an average diameter of about 700-800 nm. The aldehyde equivalent weight (CHO EW) of this fibrous polymer was 364. A scanning electron micrograph of the dextran aldehyde/dextran fibrous polymer is shown in FIG. 1.

The fibrous polymer obtained was impregnated with a branched polyethylene glycol (PEG) amine and then wet with water to effect dissolution and crosslinking to form a hydrogel via condensation of the nucleophilic PEG amine groups with electrophilic dextran aldehyde groups. Finely ground 8-arm PEG 40K hexadecaamine (27 mg), prepared as described in Reagent Preparations, was spread evenly on a 20-mg piece of the fibrous polymer, which had been stripped from its REEMAY® backing, and rubbed in. When dampened, the fibrous sheet quickly dissolved and then crosslinked slowly over 1 min to form an elastic hydrogel.

Example 2

Preparation of an Anhydrous Fibrous Sheet Comprising Dextran Aldehyde and Eight-Arm PEG 10K Octaamine (P8-10-1)

The following Example demonstrates the preparation of an anhydrous fibrous sheet comprising a fibrous polymer containing dextran aldehyde and dextran that is impregnated with 8-arm PEG 10K octaamine (P8-10-1). A solution containing dextran aldehyde and dextran was electro-blown spun into a fibrous dextran sheet, into which was added finely ground solid P8-10-1 PEG amine.

A fibrous polymer containing dextran aldehyde and dextran, was prepared as described in Example 1. Finely ground 8-arm PEG 10K octaamine (P8-10-1) was prepared as described in Reagent Preparations, and 12 mg was spread evenly on a 16-mg piece of the fibrous polymer which had been stripped from its REEMAY® backing, and rubbed in. When dampened with deionized water, the fibrous sheet became a soft, tacky, elastic hydrogel in 5-10 sec.

Example 3

Preparation of an Anhydrous Fibrous Sheet Comprising Dextran Aldehyde and Eight-Arm PEG 10K Octaamine (P8-10-1)

The following Example demonstrates the preparation of an anhydrous fibrous sheet comprising a fibrous polymer containing dextran aldehyde and dextran that is impregnated with 8-arm PEG 10K octaamine (P8-10-1). A solution containing dextran aldehyde and dextran was electro-blown spun into a fibrous dextran sheet, which was wetted with a solution containing the P8-10-1 PEG amine in dichloromethane.

A 52-mg (3 cm×3 cm) piece of the fibrous dextran aldehyde sheet, prepared as described in Example 1, which had been stripped from its REEMAY® backing, was placed in an aluminum weighing pan and wetted evenly dropwise with 0.37 g of a solution containing 1.00 g of P8-10-1 in 5 mL (6.5 g) of dichloromethane (13 wt % P8-10-1). The damp sheet was quickly dried under a nitrogen stream. About 50 mg of P8-10-1 was deposited on the fibers ($CHO:NH_2$=3.8). The originally soft, flexible sheet was now stiffer, like cardstock. When it was placed in a drop of water, the fibrous sheet quickly wetted but maintained its shape and crosslinked to a slightly tacky and somewhat elastic translucent hydrogel.

Example 4

Tissue Adhesion of a Fibrous Sheet Comprising Dextran Aldehyde and Eight-Arm PEG 10K Octaamine (P8-10-1)

The following Example demonstrates the adhesion of a hydrogel formed by wetting an anhydrous fibrous sheet comprising dextran aldehyde and 8-arm PEG 10K octaamine (P8-10-1) to a swine uterine horn.

Clean, fresh swine uterine horn was obtained from a local grocery and was cut into approximately 2-3-inch (5.1-7.6 cm) sections for tissue adhesion testing. The sections were stored frozen and were thawed just before use.

A 47-mg (2 cm×3 cm) piece of fibrous dextran aldehyde sheet, prepared as described in Example 1, which had been stripped from its REEMAY® backing, was placed in an aluminum weighing pan, wetted evenly with 0.45 g of a solution of 1.00 g P8-10-1 PEG amine in 5.0 mL dichloromethane and quickly dried under a nitrogen stream. About 60 mg of the PEG amine was deposited on the fibers ($CHO:NH_2$=3.2). A 1-cm×1-cm section of the fibrous sheet was laid on a 2-inch (5.1 cm) section of damp swine uterine horn and lightly misted with water to completely wet it. After wetting, the sheet formed an adherent, translucent hydrogel patch. After a period of 1 min, the uterine horn was stretched from the ends to test the adhesion of the hydrogel patch. The thin patch stretched with the uterine horn and did not peel up. Testing by applying a force at the edges of the patch or scraping it lightly with a spatula also did not dislodge the patch, indicating that it was well-adhered. The experiment was repeated with another piece of fibrous sheet and another piece of swine uterine horn with the same results, i.e., adhesion was very good and the patch did not seem particularly fragile.

The sections of swine uterine horn with the hydrogel patches on them were soaked in a pan of water at room temperature for 35 min. The patches swelled but did not dislodge and were still well-adhered, although they became rather soft. Scraping with a spatula at the edges of the patch broke off small pieces of hydrogel, but the patch did not peel off.

Examples 5 and 6

Sealing an Incision in a Swine Uterine Horn Using a Fibrous Sheet Comprising Dextran Aldehyde and Eight-Arm PEG 10K Octaamine (P8-10-1)

The following Examples demonstrate the use of fibrous sheets comprising dextran aldehyde and 8-arm PEG 10K octaamine (P8-10-1) to seal an incision in a swine uterine horn. A fibrous dextran aldehyde sheet was impregnated with P8-10-1 PEG amine at two different levels and the two resulting fibrous sheets were used to seal an incision in a swine uterine horn.

A 12-cm×18-cm sheet (1.8 g) of a fibrous dextran aldehyde sheet, prepared as described in Example 1, which had been stripped from its REEMAY® backing was placed in a shallow aluminum pan. The sheet was thoroughly wetted with 20 g of a solution of 10 wt % 8-arm PEG 10K octaamine (P8-10-1) in dichloromethane ($CHO:NH_2$=3.3). The pan with the wetted sheet was promptly placed in a large sealed, plastic bag to prevent condensation of moisture from the air and the sheet was dried under a stream of nitrogen from a hose placed into the bag for 10 min. The impregnated fibrous sheet was then placed under high vacuum and evacuated for 1 hour, producing a stiff, rather friable dry sheet. The sheet was stored in a nitrogen-filled, sealed plastic bag. This fibrous sheet was used in Example 5.

A second 12-cm×18-cm sheet (2.5 g) of the fibrous dextran aldehyde sheet, prepared as described in Example 1, which had been stripped from its REEMAY® backing was placed in a shallow aluminum pan lined with a PTFE sheet. The fibrous dextran aldehyde sheet was thoroughly wetted with 20 g of a solution of 10 wt % 8-arm PEG 10K octaamine (P8-10-1) in dichloromethane ($CHO:NH_2$=4.5) and dried under nitrogen and vacuum as described above. This fibrous sheet was used in Example 6.

The two fibrous sheets were cut into 1.5-cm×3-cm (0.13-0.16 g) rectangular patches. The smoother topside of the patch (away from the original REEMAY® support) was usually applied to the tissue. A 1-cm transverse incision was made with scissors in the center of a 2-inch (5.1 cm) section of fresh swine uterine horn and the uterine horn was connected with a nylon tie to the nipple of a feed line from a syringe pump with a pressure gauge; the other end of the uterine horn was closed with a hemostat clamp. The syringes were filled with dyed water. The uterine horn was dampened and a piece of anhydrous fibrous sheet was pressed firmly over the incision and then was dampened with one squirt of water from a spray mister to dissolve the fibers and form the hydrogel patch, which immediately became limp and conformed to the contours of the tissue. After 2 min, the patched uterine horn was immersed in a large pan of water and water pressure was applied via the syringe pump until the patch leaked as evidenced by a stream of dye from the patched area of the uterine horn. The mean leak pressures and standard deviations are given in Table 1. In general, adhesion of the hydrogel patch to the uterine horn was excellent; about half the failures were due to edge leaks around the highly-curved mesentery side of the uterine horn. If no patch was placed on the incision, the leak pressure was <0.1 psig (<0.7 kPa).

TABLE 1

Leak Pressures of Sealed Incisions in Swine Uterine Horn

| Example | Number of Trials | Leak Pressure, psig |
| --- | --- | --- |
| 5 | 11 | 0.66 ± 0.13 (4.6 ± 0.9 kPa) |
| 6 | 24 | 0.77 ± 0.05 (5.3 ± 0.3 kPa) |

The swine uterine horn sealing experiments described above were repeated using two fibrous sheets of Example 5, one applied over the other. The mean leak pressure was 1.23±0.32 psig (8.5±2.2 kPa) for three trials.

These results demonstrate that the anhydrous fibrous sheets containing dextran aldehyde and P8-10-1 PEG amine are effective in sealing incisions in swine uterine horn and suggest that the fibrous sheets would be useful as a tissue adhesive and sealant.

Example 7

Preparation of an Anhydrous Fibrous Sheet Comprising Dextran Aldehyde and Four-Arm PEG K Tetraamine (P4-2-1)

The following Example demonstrates the preparation of an anhydrous fibrous sheet comprising dextran aldehyde and a 4-arm PEG 2K tetraamine (P4-2-1). A solution containing dextran aldehyde and dextran was electro-blown spun into a fibrous dextran aldehyde sheet, which was coated with a solution containing P4-2-1.

A fibrous dextran aldehyde sheet was prepared as follows. A solution of 20.0 g dextran aldehyde solution containing 25 wt % of D10-50 (($M_w$=10 kDa; oxidation level=50% of glucose rings cleaved to dialdehydes; prepared as described in Reagent Preparations) in water and 5 g of dextran 100K ($M_w$=100 kDa; Aldrich D4876) was prepared and allowed to stand for 2 hours, at which point it gelled. With the addition of 3 g of water and stirring the gel at room temperature for 2 hours, a flowable viscous solution was obtained. This dextran solution contained 18 wt % D10-50 and 18 wt % dextran 100K.

The dextran solution was electro-blown spun at 100 kV according to the method described in Example 1 to form a fibrous dextran sheet about a millimeter thick, which contained 50 wt % dextran aldehyde and 50 wt % dextran 100K (CHO EW=292). The fiber diameter was on the order of 2-3 µm.

A 25-g sample of 4-arm PEG 2K tetraamine, prepared as described in Reagent Preparations, was combined with 100 mL of toluene and the solution was rotary evaporated under vacuum pump aspiration (about 3 mm Hg, 0.4 kPa) from a hot water bath (80° C.) to azeotrope off water. After toluene stopped distilling off, the vacuum and heat source were interrupted and the flask was held in the water bath under a nitrogen stream as it slowly cooled. The yield of 4-arm PEG 2K tetraamine was 25.3 g; so the PEG amine contains about 1 wt % residual toluene. The flask of 4-arm PEG 2K tetraamine was transferred into a nitrogen-filled glove box, rebottled, and stored and used in the box to avoid moisture uptake.

The fibrous dextran aldehyde sheet was coated with P4-2-1 PEG amine as follows. Two 4 inch×12 inch (10.2 cm×30.5 cm) sheets of the fibrous dextran sheet were rolled up in a cylindrical vacuum flask and were held under high vacuum (0.05 mm of mercury, 6.7 Pa) at room temperature for 18 hours in an attempt to rigorously dry the fibers. The flask was transferred to a nitrogen-filled glove box still under vacuum and the fibrous dextran aldehyde sheets were removed and transferred to sealed plastic bags in the glove box.

A 8-cm×10-cm sheet (0.71 g) of the dried fibrous dextran aldehyde sheet, which had been stripped from its REEMAY® backing, was placed in a shallow aluminum pan lined with a PTFE sheet. The fibrous dextran aldehyde sheet was thoroughly wetted with a solution of 0.3 g of dried 4-arm PEG 2K tetraamine in 12 mL of dichloromethane ($CHO:NH_2$=4.0). The wet fibrous sheet was dried under a stream of nitrogen for 15 min and the pan was then placed in a vacuum chamber and evacuated for 40 min. This produced a soft, dry-appearing fibrous sheet resembling the original fibrous dextran sheet. The fibrous sheet was stored in a sealed plastic bag under nitrogen in the glove box until use.

Examples 8 and 9

Sealing an Incision in a Swine Uterine Horn Using a Fibrous Sheet Comprising Dextran Aldehyde and Four-Arm PEG Tetraamine (P4-2-1)

The following Examples demonstrate the use of an anhydrous fibrous sheet comprising dextran aldehyde and 4-arm PEG 2K tetraamine (P4-2-1) to seal an incision in a swine uterine horn.

The anhydrous fibrous sheet described in Example 7 was cut into 2-cm×3-cm rectangular patches, each weighing about 0.06-0.09 g. The smoother topside of the patch away from the original REEMAY® backing was usually applied to the tissue because this side may be somewhat more aldehyde-rich as the PEG amine may concentrate at the bottom during impregnation and evaporation. It is believed that placing the aldehyde-rich side of the fibrous sheet in contact with the tissue may increase adhesion due to the interaction of the aldehyde groups with free amine groups on the tissue.

This anhydrous fibrous sheet was used to seal a swine uterine horn, as described in Examples 6 and 7. Fibrous sheets were lightly pressed onto the damp swine uterine horn over a 1-cm incision and lightly tamped down around the perimeter to help establish a bond to the tissue. Then, the sheet was misted with a plant mister to wet it completely (Example 8). When a second sheet was used (Example 9), it was immediately applied over the first patch in the same manner. The sheet was allowed to crosslink for a minute before immersing in water and pressure testing. The results of the pressure testing are summarized in Table 2.

TABLE 2

Leak Pressures of Sealed Incisions in Swine Uterine Horn

| Example | Number of Fibrous Sheets | Number of Trials | Leak Pressure, psig |
| --- | --- | --- | --- |
| 8 | 1 | 2 | 0.42 ± 0.20 (2.9 ± 1.4 kPa) |
| 9 | 2 | 6 | 0.80 ± 0.27 (5.5 ± 1.9 kPa) |

The results demonstrate that the anhydrous fibrous sheets containing dextran aldehyde and P4-2-1 PEG amine were effective in sealing incisions in swine uterine horn and suggest that the fibrous sheets would be useful as a tissue adhesive and sealant.

Example 10

Preparation of an Anhydrous Fibrous Sheet Comprising Poly(vinyl alcohol-co-vinyl amine) and Four-Arm PEG 2K tetra(thiomethylaldehyde)

The following Example demonstrates the preparation of an anhydrous fibrous sheet comprising poly(vinyl alcohol-co-vinyl amine) and 4-arm PEG 2K tetra(thiomethylaldehyde). A solution containing poly(vinyl alcohol-co-vinyl amine) was electro-blown spun into a fibrous polymer sheet, which was coated with solution containing 4-arm PEG 2K tetra (thiomethylaldehyde).

Figure 2:
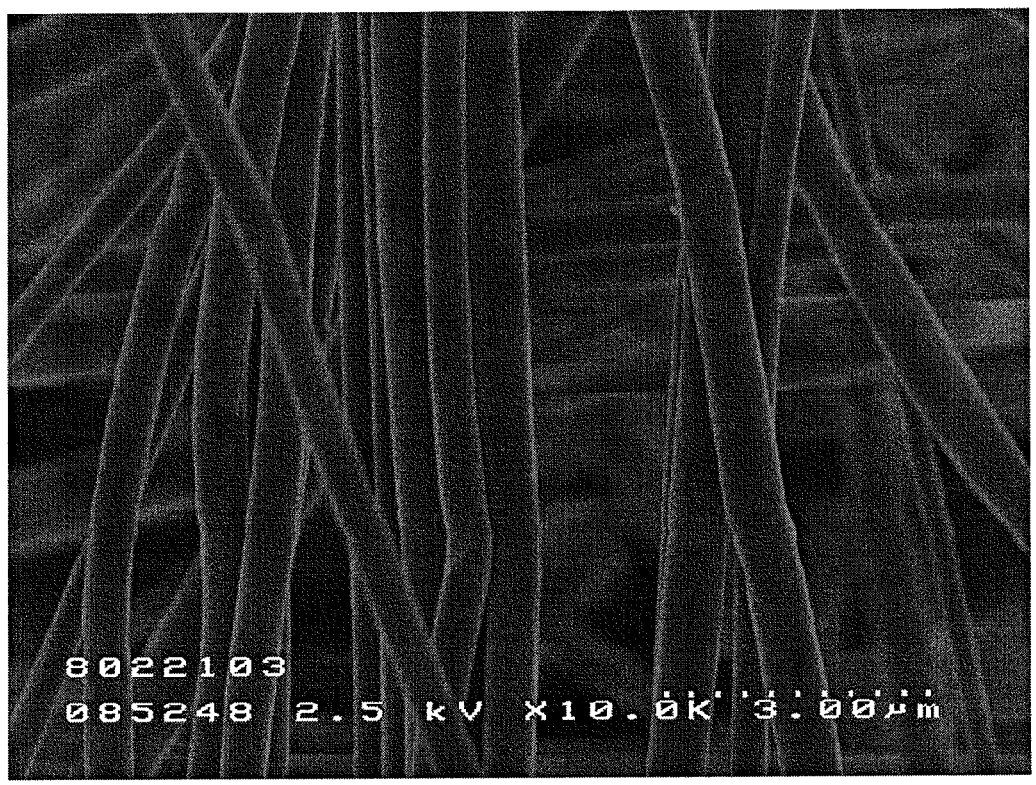
FIG. 2 is a scanning electron micrograph of the poly(vinyl alcohol-co-vinyl amine) fibrous polymer described in Example 10.

A solution containing 20 wt % of poly(vinyl alcohol-co-vinyl amine), prepared as described in Reagent Preparations Method A, was electro-blown spun at 100 kV under conditions similar to those given in Example 1 to give a fibrous polymer sheet about a millimeter thick having a fiber diameter of about 1-3 μm. A scanning electron micrograph of the poly(vinyl alcohol-co-vinyl amine) fibrous polymer is shown in FIG. 2. This fibrous poly(vinyl alcohol-co-vinyl amine) polymer sheet was stored in a nitrogen-filled glove box and kept protected from atmospheric carbon dioxide. The sheet was very hydrophilic and would cling tenaciously to one's hands if they were even slightly damp.

A 10-cm×12-cm sheet (0.75 g) of the poly(vinyl alcohol-co-vinyl amine) fibrous polymer, which had been stripped from its REEMAY® backing, was placed in a shallow aluminum pan lined with a PTFE sheet. The pan was placed in a nitrogen-filled glove box, and the fibrous sheet was thoroughly wetted with a solution of 0.30 g 4-arm PEG 2K tetra (thiomethylaldehyde), prepared as described in Reagent Preparations, in 10 mL of dichloromethane (CHO: $NH_2$=0.31). The wetted sheet was dried under a stream of nitrogen for 15 min and the pan was then placed in a vacuum chamber and evacuated for 20 min, producing a soft, dry-appearing sheet resembling the original fibrous poly(vinyl alcohol-co-vinyl amine) polymer sheet. The fibrous sheet comprising poly(vinyl alcohol-co-vinyl amine) and the four-arm PEG 2K tetra(thiomethylaldehyde) was stored in a sealed plastic bag under nitrogen in the glove box until use.

Example 11

Sealing an Incision in a Swine Uterine Horn Using a Fibrous Sheet Comprising Poly(vinyl alcohol-co-vinyl amine) and Four-Arm PEG 2K Tetra(thiomethylaldehyde)

The following Example demonstrates the use of an anhydrous fibrous sheet comprising poly(vinyl alcohol-co-vinyl amine) and 4-arm PEG 2K tetra(thiomethylaldehyde) to seal an incision in a swine uterine horn.

The fibrous sheet comprising poly(vinyl alcohol-co-vinyl amine) and 4-arm PEG 2K tetra(thiomethylaldehyde), prepared as described in Example 10, was cut into 1.5-cm×2-cm rectangular patches. The weights of the patches were about 50-60 mg. The smoother topside of the patch was always applied to the tissue for reasons described in Examples 8 and 9. This fibrous sheet was used to seal an incision in a swine uterine horn, as described in Examples 5 and 6. A single patch was lightly pressed onto the damp swine uterine horn over a 1-cm incision and lightly tamped down around the perimeter to help establish a bond to tissue and then allowed to cure for 1 min before pressure testing. The patches were typically not wetted further with a mister after application.

The mean leak pressure for ten trials in this test was 1.79±1.30 psig (12.3±9.0 kPa). This result demonstrates that the anhydrous fibrous sheet comprising poly(vinyl alcohol-co-vinyl amine) and 4-arm PEG 2K tetra(thiomethylaldehyde) is effective in sealing incisions in swine uterine horn and suggests that the fibrous sheet would be useful as a tissue adhesive and sealant.

Example 12

Preparation of an Anhydrous Fibrous Sheet Comprising Poly(vinyl alcohol-co-vinyl amine) and PEG 600 Bis(thiomethylaldehyde)

The following Example demonstrates the preparation of an anhydrous fibrous sheet comprising poly(vinyl alcohol-co-vinyl amine) and PEG 600 bis(thiomethylaldehyde). A solution containing poly(vinyl alcohol-co-vinyl amine) was electro-blown spun into a fibrous polymer sheet, which was coated with a solution containing PEG 600 bis(thiomethylaldehyde).

An 8-cm×10-cm sheet (0.48 g) of the poly(vinyl alcohol-co-vinyl amine) fibrous polymer sheet, described in Example 10, which had been stripped from its REEMAY® backing, was placed in a shallow aluminum pan lined with a PTFE sheet. The pan was placed in a nitrogen-filled glove box, and the fibrous sheet was thoroughly wetted with a solution of 0.18 g PEG 600 bis(thiomethylaldehyde), prepared as described in Reagent Preparations, in 10 mL of dichloromethane (CHO:$NH_2$=0.49). The wetted sheet was dried under a stream of nitrogen for 15 min and the pan was then placed in a vacuum chamber and evacuated for 10 min, producing a soft, dry-appearing sheet resembling the original sheet of poly(vinyl alcohol-co-vinyl amine) fibrous polymer. The sheet was stored in a sealed plastic bag under nitrogen in the glove box until use.

Example 13

Preparation of an Anhydrous Fibrous Sheet Comprising Poly(vinyl alcohol-co-vinyl amine) and PEG 600 Bis(thiomethylaldehyde)

The following Example demonstrates the preparation of an anhydrous fibrous sheet comprising poly(vinyl alcohol-co-vinyl amine) and PEG 600 bis(thiomethylaldehyde). A solution containing poly(vinyl alcohol-co-vinyl amine) was electro-blown spun into a fibrous polymer sheet, which was coated with a solution containing PEG 600 bis(thiomethylaldehyde).

A 7-cm×10-cm sheet (0.43 g) of the poly(vinyl alcohol-co-vinyl amine) fibrous polymer sheet, described in Example 10, which had been stripped from its REEMAY® backing, was placed in a shallow aluminum pan lined with a PTFE sheet. The pan was placed in a nitrogen-filled glove box, and the fibrous sheet was thoroughly wetted with a solution of 0.25 g PEG 600 bis(thiomethylaldehyde), prepared as described in Reagent Preparations, in 10 mL of dichloromethane (CHO:$NH_2$=0.76). The wetted sheet was dried under a stream of nitrogen for 15 min and the pan was then placed in a vacuum chamber and evacuated for 10 min, producing a soft, dry-appearing sheet resembling the original sheet of poly(vinyl alcohol-co-vinyl amine) fibrous polymer. The sheet was stored in a sealed plastic bag under nitrogen in the glove box until use.

Examples 14 and 15

Sealing an Incision in a Swine Uterine Horn using Fibrous Sheets Comprising PolyCvinyl alcohol-co-vinyl amine) and and PEG 600 Bis(thiomethylaldehyde)

The following Examples demonstrate the use of anhydrous fibrous sheets comprising poly(vinyl alcohol-co-vinyl amine) and PEG 600 bis(thiomethylaldehyde) to seal an incision in a swine uterine horn.

The anhydrous fibrous sheets described in Examples 12 and 13 were subjected to the swine uterine horn burst test described in Examples 5 and 6. The fibrous sheets were cut into 1.5-cm×2-cm rectangular pieces. The weights of most of the rectangles were about 60 mg, but there were also some thin patches of about 20-30 mg. The smoother topside of the patch away from the original REEMAY® support was always applied to the tissue. A single patch was lightly pressed onto the damp swine uterine horn over the 1-cm incision and lightly tamped down around the perimeter to help establish a bond to the tissue and allowed to cure for 60 sec before pressure testing. The patches were not wetted further with a mister after application. In a few experiments, the patch was pressed onto the damp tissue and then the uterine horn section was immediately immersed in water for 60 sec while the patch cured. Burst pressures were as high in those cases as when the patch was cured in air. The mean leak pressures and standard deviations are given in Table 3.

TABLE 3

Leak Pressures of Sealed Incisions in Swine Uterine Horn

| Example | Fibrous Sheet | Number of Trials | Leak Pressure, psig |
|---|---|---|---|
| 14 | from Example 12 | 10 | 2.17 ± 1.17 (15.0 ± 8.1 kPa) |
| 15 | from Example 13 | 8 | 1.39 ± 0.91 (9.58 ± 6.27 kPa) |

The results demonstrate that the anhydrous fibrous sheets containing poly(vinyl alcohol-co-vinyl amine) and PEG 600 bis(thiomethylaldehyde) were effective in sealing incisions in swine uterine horn and suggest that the fibrous sheets would be useful as a tissue adhesive and sealant. Adhesion was good in all cases and better than cohesion. A trace of hydrogel adhesive remained on the tissue when a patch was pulled off. The lower PEG 600 bis(thiomethylaldehyde) loading appeared to give higher burst pressures (Example 14) than higher loading (Example 15). Leaks were typically at the edges, due to failure of the patch to conform to the highly-curved tissue surface. It is important for the patch to be in intimate contact with the tissue while it is initially being wetted for good adhesion at the edges. The thinner patches, while lacking the cohesive strength of the thicker patches, conformed and adhered very well to curved tissue surfaces.

Example 16

Preparation of an Anhydrous Fibrous Sheet Comprising Dextran Aldehyde and Dextran Acetoacetate The following Example demonstrates the preparation of an anhydrous fibrous sheet comprising dextran aldehyde and dextran acetoacetate. The fibrous sheet was formed by electro-blown spinning a solution containing a mixture of both components.

A mixture of 15 g dextran aldehyde solution containing 25 wt % of D10-48 (prepared as described in Reagent Preparations) in water and 5 g of dextran acetoacetate, prepared as described in Reagent Preparations, containing 3 drops of acetic acid to forestall condensation was prepared. The mixture initially gave a viscous solution but soon became a gel. Stirring and heating with 5 g of water gave a solution which began to gel again on cooling (omitting the acetic acid resulted in a crosslinked gel which did not dissolve in excess water and did not liquefy on warming). Rewarming the mixture gave a fluid, spinnable solution which contained 15 wt % D10-48 and 20 wt % dextran acetoacetate. This solution was electro-blown spun into fibers, as described in Example 1. The fiber plume was narrower than with the solution of Example 1. Although the polymer apparently was not taking on as much charge, it still spun well. The average fiber diameter was about 1600 nm (1.6 μm). The fibrous sheet contained 33 wt % D10-48 and 67 wt % dextran acetoacetate, and was a few mm thick but was very easily compacted with handling, e.g., upon applying pressure, the sheet flattened to a thickness of about 0.01 inches (0.25 mm). The fibrous sheet had reasonable strength and could be handled without tearing, although it could be torn without difficulty. The sheet was very hydrophilic and would cling tenaciously to one's hands if they were even slightly damp.

The fibrous sheet comprising dextran aldehyde and dextran acetoacetate was treated with aqueous base to effect dissolution and crosslinking to a hydrogel via condensation of the nucleophilic conjugate base of the acidic acetoacetate methylenes with electrophilic dextran aldehyde groups. Specifically, upon spraying a piece of the fibrous sheet, which had been stripped from its REEMAY® backing, with an aqueous solution containing 10 wt % sodium carbonate, the dampened fibrous sheet became translucent but retained its shape as a result of crosslinking to form a friable, unswollen hydrogel.

Spraying the fibrous sheet as described above, but using a dilute sodium carbonate solution (i.e., 0.2 wt %) for wetting resulted in the formation of a clear, crosslinked hydrogel which was slightly swollen. The fibrous sheet retained its shape and could be handled somewhat but was rather weak.

Spraying the fibrous sheet as described above, but using water or aqueous phosphate buffer (pH 7.4) for wetting did not result in the formation of a crosslinked hydrogel because a stronger base is required to form the nucleophilic conjugate base of acetoacetate to react with the electrophilic dextran aldehyde groups.

Additionally, finely ground sodium bicarbonate (20 mg) was spread evenly on a 23-mg piece of the fibrous sheet containing dextran aldehyde and dextran acetoacetate, which had been stripped from its REEMAY® backing, and rubbed in. When dampened with water, the fibrous sheet became translucent, but maintained its shape as a stiff, weak hydrogel.

Example 17

Preparation of an Anhydrous Fibrous Sheet Comprising Fibrous Dextran Aldehyde and Fibrous Poly(vinyl alcohol-co-vinyl amine)

The following Example demonstrates the preparation of an anhydrous bilayer fibrous sheet comprising a layer of nucleophilic poly(vinyl alcohol-co-vinyl amine) fiber and a layer of electrophilic dextran aldehyde/dextran 100K fiber.

A mixture of 10 g of poly(vinyl alcohol-co-vinyl amine) polymer, prepared as described in Reagent Preparations, Method B, and 45 g of deionized water was stirred at 70° C. in a water bath for 2 hours to give a viscous solution containing 18 wt % of the polymer. This solution was used to spin the poly(vinyl alcohol-co-vinyl amine) polymer into a fibrous sheet.

A mixture of 30 g of a dextran aldehyde solution (D10-50, 25 wt %) (starting dextran $M_w$=10 kDa; 50 mol % of the glucose rings were oxidized to dialdehydes) and 9 g of dextran100K ($M_w$=100 kDa; Aldrich D4876) was stirred at room temperature for 10 min and then 6 g water was added and the solution was stirred 5 min more. The solution contained 17 wt % D10-50 and 20 wt % dextran100K; 37 wt % total solids. The solid fiber spun from this solution had the composition D10-50 dextran aldehyde 46 wt %/dextran 100 kDa 54 wt % (CHO EW=340).

In the electro-blown spinning apparatus, described in Example 1, the total takeup drum area covered by the REEMAY® backing was about 1900 cm². The aim was to lay down a layer of each polymer fiber about 1 mg/cm² thick, which is equivalent to about 2 g total of each polymer fiber over this area. For an 18 wt % solution of poly(vinyl alcohol-co-vinyl amine) with a density of about 1.2, around 10 mL of solution had to be spun to give a 1 mg/cm² fibrous sheet. For a 37 wt % solution of dextran aldehyde/dextran 100K with similar density, about 5 mL of solution was needed to be spun to give a 1 mg/cm² fibrous sheet. The takeup drum was moved to the lower position (36 cm away from orifice) to improve the distribution of the fiber over the REEMAY® support. A layer of fiber from 10 mL of 18 wt % poly(vinyl alcohol-co-vinyl amine) solution was electro-blown spun onto the drum over 25 min at 120 psig (827 kPa) followed by a layer of fiber electro-blown spun from 5 mL of 37 wt % dextran aldehyde/dextran 100K solution over about 4 min at 40 psig (276 kPa). This bilayer fibrous sheet had a CHO:NH$_2$ ratio=1.15. The fibrous sheet was stored in a sealed, plastic bag in a nitrogen-filled glove box until use.

Examples 18 and 19

Sealing an Incision in a Swine Uterine Horn using Fibrous Sheets Comprising Poly(vinyl alcohol-co-vinyl amine) and Dextran Aldehyde The following Examples demonstrate the use of anhydrous fibrous sheets comprising alternating layers of fibrous poly (vinyl alcohol-co-vinyl amine) and fibrous dextran aldehyde to seal an incision in a swine uterine horn.

A 2.5-cm×37-cm (93 cm²) section from the center of the bilayer fibrous sheet comprising poly(vinyl alcohol-co-vinyl amine) and dextran aldehyde/dextran 100K, described in Example 17, was stripped from the REEMAY® backing. The fibrous sheet weighed 200 mg, and although the sheet was not quite uniform in thickness, this is equivalent to about 2.2 mg/cm². This strip of fibrous sheet was cut in the middle into two strips the same width and half the original length, and the two strips were individually wound around a 1.8-cm diameter rod. The wound-up rolls were each slit in the transverse direction with a razor blade and flattened out into 2.5-cm×6-cm layered sheets that were comprised of three or four layers of alternating poly(vinyl alcohol-co-vinyl amine) and dextran aldehyde/dextran 100K. Each multilayered sheet was cut into three 2.5-cm×2-cm rectangular pieces weighing about 30 mg. In Example 18, a single piece of the multilayered fibrous sheet was used to seal an incision in a swine uterine horn as described in Examples 5 and 6.

Another 2-cm×37-cm section from the center of the bilayer fibrous sheet comprising poly(vinyl alcohol-co-vinyl amine) and dextran aldehyde/dextran 100K, described in Example 17, was stripped from the REEMAY® backing and cut into 1.5-cm×2-cm patches; each of these patches weighed only about 6 mg. In Example 19, four or five of these single-thickness bilayer patches were applied on top of one another over an incision in a swine uterine horn to build up a multilayer patch which was subjected to the swine uterine horn burst test described in Examples 5 and 6.

In the burst testing, the fibrous patch was firmly pressed, amine side down (i.e., with the poly(vinyl alcohol-co-vinyl amine) fiber face exposed to the tissue surface), onto the damp swine uterine horn over the 1-cm incision and the edges were tamped down with a dry spatula to effect a seal. When the multilayer patch of Example 18 was used, the patch on the uterine horn was misted with water to wet it through and then it was allowed to cure for 60 sec before immersing the swine uterine horn in water and pressure testing. When the single-thickness, bilayer fibrous patch of Example 19 was used to build up a multilayer, the first patch was pressed onto the damp tissue amine side down. When the first patch had absorbed enough water to wet through, the next patch was applied, also amine side down, with no or minimal additional dampening. In this way a multilayer structure of 4 or 5 patches was built up, misting with water only after every other patch application. Care was taken to interface opposite fiber layers when building up a multilayer patch to optimize crosslinking; i.e., dextran aldehyde fiber was applied facing poly(vinyl alcohol-co-vinyl amine) fiber. The patches were allowed to cure 60 sec before immersing in water and pressure testing. The results of the pressure testing are summarized in Table 4.

TABLE 4

Leak Pressures of Sealed Incisions in Swine Uterine Horn

| Example | Number of Fibrous Patches | Number of Trials | Leak Pressure, psig |
|---|---|---|---|
| 18 | 1 multilayer | 5 | 0.38 ± 0.15 (2.6 ± 1.0 kPa) |
| 19 | 4-5 single bilayer | 4 | 0.52 ± 0.13 (3.6 ± 0.9 kPa) |

The results demonstrate that the anhydrous fibrous sheets comprising alternating layers of fibrous poly(vinyl alcohol-co-vinyl amine) and fibrous dextran aldehyde were effective in sealing incisions in swine uterine horn and suggest that the fibrous sheets would be useful as a tissue adhesive and sealant.

Example 20

Preparation of an Anhydrous Fibrous Sheet Comprising Poly(vinyl alcohol-co-vinyl amine) and Linear PEG 600 Diisocyanate The following Example demonstrates the preparation of an anhydrous fibrous sheet comprising poly(vinyl alcohol-co-vinyl amine) and PEG 600 diisocyanate. A solution containing poly(vinyl alcohol-co-vinyl amine) was electro-blown spun into a fibrous polymer sheet, which was coated with a solution containing PEG 600 diisocyanate.

A poly(vinyl alcohol-co-vinyl amine) polymer was prepared according to Method B in the Reagent Preparation section above, except no chain transfer agent was employed. This provided a higher molecular weight poly(vinyl alcoholco-vinyl amine) ($M_w$=1000K) with about 10 mol % amine. A 12 wt % solution of this poly(vinyl alcohol-co-vinyl amine) solution was electro-blown spun, using the apparatus described in Example 1, at 100 kV using a solution feed rate of 0.5 mL/min to give a fibrous polymer sheet having a fiber diameter of about 0.5-1 μm. The distance from the orfice to the drum was about 40 cm in the electro-blown spinning process. The resulting poly(vinyl alcohol-co-vinyl amine) fibrous polymer sheet was stored in a nitrogen-filled glove box and kept protected from atmospheric carbon dioxide.

A 7-cm×10-cm sheet (0.22 g, the sheet was thin compared to other fibrous sheets tested in the previous Examples) of the poly(vinyl alcohol-co-vinyl amine) fibrous polymer sheet which had been stripped from its Reemay® backing was placed in a shallow aluminum pan that had been lined with a PTFE sheet. The pan was placed in a nitrogen-filled glove box, and the sheet was thoroughly wetted with a solution of 0.10 g PEG 600 diisocyanate, prepared as described in Reagent Preparation, in 10 mL of dichloromethane (NCO:$NH_2$=0.67). The wet sheet was dried under a stream of nitrogen for 15 min and the pan was then placed in a vacuum chamber and evacuated for 10 min. This produced a soft, dry-appearing sheet resembling the original fibrous polymer sheet. The sheet was stored in a sealed plastic bag under nitrogen in the glove box until use.

Example 21

Sealing an Incision in a Swine Uterine Horn with an Anhydrous Fibrous Sheet Comprising Polyvinyl alcohol-co-vinyl amine) and PEG 600 Diisocyanate The following Example demonstrates the use of an anhydrous fibrous sheet comprising poly(vinyl alcohol-co-vinyl amine) and PEG 600 diisocyanate to seal an incision in a swine uterine horn.

The anhydrous fibrous sheet comprising poly(vinyl alcohol-co-vinyl amine) and PEG 600 diisocyanate, described in Example 20, was subjected to the swine uterine horn burst test described in Examples 5 and 6. The sheets were cut into 1.5-cm×2-cm rectangular pieces. The weight of most of the rectangles was about 15 mg. A single patch was lightly pressed onto the damp swine uterine horn over the 1-cm incision and lightly tamped down around the perimeter to help establish a bond to tissue, misted once and allowed to cure 60 sec before pressure testing. Adhesion was excellent in all cases and burst pressures were high despite the thin patches, specifically, the mean leak pressure for two trials was 3.70 ±0.28 psig (25.5 ±1.93 kPa).

Example 22

Preparation of an Anhydrous Fibrous Sheet Comprising Dextran Aldehyde of Two Different Molecular Weights and Eight-Arm PEG 10K Octaamine (P8-10-1)

The following Example demonstrates the preparation of an anhydrous fibrous sheet comprising a fibrous polymer containing dextran aldehyde of two different molecular weights that is impregnated with 8-arm PEG 10K octaamine (P8-10-1) by wetting with a solution containing the P8-10-1 PEG amine in dichloromethane.

A fibrous polymer sheet containing dextran aldehyde of two different molecular weights was prepared as follows. A mixture of 20 g of dextran aldehyde solution containing 25 wt % of D10-50 (prepared as described in Reagent Preparations) in water and 3 g of solid dextran aldehyde D100-6 (prepared as described in Reagent Preparations) was prepared by stirring the two components at 45° C. for an hour. The resulting clear solution was then allowed to stand at room temperature for 30 min before spinning. This solution was electro-blown spun into fibers, as described in Example 1. Upon spinning at 10-20 psig feed pressure and 4 psig jet pressure, the solution gave fine, short fibers (<1 cm) which laid down to give a fine felt. The average fiber diameter was 350-700 nm. The fibrous sheet contained 63 wt % D10-50 and 37 wt % dextran aldehyde D100-6.

A 331-mg piece of the fibrous dextran aldehyde polymer sheet, prepared as described above, which had been stripped from its REEMAY® backing, was placed in an aluminum weighing pan and wetted evenly dropwise with a solution of 0.28 g of P8-10-1 in 3 mL of dichloromethane. The damp sheet was dried under a nitrogen stream to give a composition with CHO:$NH_2$=7.0.

Example 23

Tissue Adhesion of a Fibrous Sheet Comprising Dextran Aldehyde of Two Different Molecular Weights and 8-arm PEG 10K Octaamine on Swine Uterine Horn A 1-cm×2-cm section of the fibrous sheet described in Example 22 was laid on a 2-inch (5 cm) section of damp swine uterine horn and lightly misted with water to completely wet it. After wetting, the sheet formed an adherent, translucent hydrogel patch. Testing by applying a force at the edges of the patch or scraping it lightly with a spatula also did not dislodge the patch, indicating that it was well-adhered. Tissue adhesion in the present case appeared superior to the corresponding composition of Example 4 in which the high molecular weight dextran component was unfunctionalized. This improvement may be due to the fact that the high molecular weight dextran component in the fibrous sheet of Example 22 is functionalized with a low level of aldehyde groups and is thus able to participate in the crosslinked structure of the hydrogel.

What is claimed is:

1. An anhydrous fibrous sheet comprising
a first component and a second component, wherein the first and second components are un-crosslinked and co-reactive with each other under physiological conditions, wherein the first component is a fibrous polymer, said polymer containing electrophilic groups or nucleophilic groups, and
the second component is capable of crosslinking the first component when said sheet is exposed to an aqueous medium in contact with biological tissue to form a crosslinked hydrogel that is adhesive to the biological tissue;
wherein the second component is a fibrous polymer having a backbone structure the same as or different from the fibrous polymer of the first component and containing electrophilic groups if the first component contains nucleophilic groups or containing nucleophilic groups if the first component contains electrophilic groups; or
the second component is a coating on the fibrous polymer of the first component, wherein said coating contains electrophilic groups if the first component contains nucleophilic groups or nucleophilic groups if the first component contains electrophilic groups; or
the second component is a dry powder dispersed and entrapped within interstices of the fibrous polymer of the first component, wherein said powder contains electrophilic groups if the first component contains nucleophilic groups or nucleophilic groups if the first component contains electrophilic groups.

2. The anhydrous fibrous sheet according to claim 1, wherein the electrophilic groups of the first component are selected from the group consisting of aldehyde, acetoacetate, and succinimidyl ester.

3. The anhydrous fibrous sheet according to claim 1, wherein the electrophilic groups of the second component are selected from the group consisting of aldehyde, acetoacetate, succinimidyl ester, and isocyanate.

4. The anhydrous fibrous sheet according to claim 1, wherein the nucleophilic groups of the first component are selected from the group consisting of primary amine, secondary amine, carboxyhydrazide, acetoacetate, and thiol.

5. The anhydrous fibrous sheet according to claim 1, wherein the nucleophilic groups of the second component are selected from the group consisting of primary amine, secondary amine, carboxyhydrazide, acetoacetate, and thiol.

6. The anhydrous fibrous sheet according to claim 1, wherein the first component comprises at least one water-dispersible polymer having electrophilic groups or nucleophilic groups and the second component comprises at least one water-dispersible polymer having nucleophilic groups when the first component is a water-dispersible polymer having electrophilic groups, or electrophilic groups when the first component is a water-dispersible polymer having nucleophilic groups.

7. The anhydrous fibrous sheet according to claim 6, wherein the first component comprises at least one water-dispersible polymer having electrophilic groups selected from the group consisting of oxidized polysaccharides having aldehyde groups, polyvinyl alcohol or polyvinyl alcohol copolymers derivatized with acetoacetate groups, and polysaccharides derivatized with acetoacetate groups.

8. The anhydrous fibrous sheet according to claim 6, wherein the second component comprises at least one water-dispersible polymer having electrophilic groups selected from the group consisting of oxidized polysaccharides having aldehyde groups, polyvinyl alcohol or polyvinyl alcohol copolymers derivatized with acetoacetate groups, polysaccharides derivatized with acetoacetate groups, linear or branched polyethers derivatized with acetoacetate groups, linear or branched polyethers derivatized with aldehyde groups, linear or branched polyethers derivatized with N-hydroxysuccinimidyl ester groups, and linear or branched polyethers derivatized with isocyanate groups.

9. The anhydrous fibrous sheet according to claim 6, wherein the first component comprises at least one water-dispersible polymer having nucleophilic groups selected from the group consisting of polyvinyl alcohol or polyvinyl alcohol copolymers having primary amine groups, secondary amine groups, or acetoacetate groups;
and polysaccharides having primary amine groups, secondary amine groups, or acetoacetate groups.

10. The anhydrous fibrous sheet according to claim 6, wherein the second component comprises at least one water-dispersible polymer having nucleophilic groups selected from the group consisting of linear or branched polyethers derivatized with primary amine groups or secondary amine groups; polyvinyl alcohol or polyvinyl alcohols copolymers having primary amine groups, secondary amine groups or acetoacetate groups; polysaccharides having primary amine groups, secondary amine groups, or acetoacetate groups; linear or branched polyethers derivatized with thiol groups; and linear or branched polyethers derivatized with carboxyhydrazide groups.

11. The anhydrous fibrous sheet according to claim 6, wherein the first component comprises at least one oxidized polysaccharide having aldehyde groups and the second component comprises at least one water-dispersible multi-arm polyether amine.

12. The anhydrous fibrous sheet according to claim 11, wherein the at least one oxidized polysaccharide is oxidized dextran and the at least one water-dispersible multi-arm polyether amine is a multi-arm polyethylene glycol amine.

13. The anhydrous fibrous sheet according to claim 1, wherein the fibrous polymer is prepared by electrospinning, electro-blown spinning, or high speed rotary sprayer spinning.

14. The anhydrous fibrous sheet according to claim 1, further comprising a non-biodegradable peelable backing or a biodegradable backing.

15. An adhesive hydrogel useful for applying a fibrous coating to an anatomical site on tissue of a living organism, wherein the adhesive hydrogel is prepared by a method comprising the steps of:
  a) applying to the site the anhydrous fibrous sheet of claim 1; and
  b) contacting the first component and the second component of the anhydrous fibrous sheet with an aqueous medium and allowing the first component and the second component to crosslink on the anatomical site to form a hydrogel that is adhesive to the tissue of the anatomical site.

16. The adhesive hydrogel according to claim 15, wherein the electrophilic groups of the first component are selected from the group consisting of aldehyde, acetoacetate, and succinimidyl ester.

17. The adhesive hydrogel according to claim 15, wherein the electrophilic groups of the second component are selected from the group consisting of aldehyde, acetoacetate, succinimidyl ester, and isocyanate.

18. The adhesive hydrogel according to claim 15, wherein the nucleophilic groups of the first component are selected from the group consisting of primary amine, secondary amine, carboxyhydrazide, acetoacetate, and thiol.

19. The adhesive hydrogel according to claim 15, wherein the nucleophilic groups of the second component are selected from the group consisting of primary amine, secondary amine, carboxyhydrazide, acetoacetate, and thiol.

20. An adhesive hydrogel useful to stanch bleeding from a surgical or traumatic wound in tissue of a living organism, the adhesive hydrogel obtained by a method comprising the steps of:
  a) applying to the wound the anhydrous fibrous sheet of claim 1, and
  b) allowing the sheet to hydrate by absorbing blood, whereby the first component and the second component crosslink to form a hydrogel that is adhesive to the tissue.

21. The adhesive hydrogel according to claim 20, wherein the electrophilic groups of the first component are selected from the group consisting of aldehyde, acetoacetate, and succinimidyl ester.

22. The adhesive hydrogel according to claim 20, wherein the electrophilic groups of the second component are selected from the group consisting of aldehyde, acetoacetate, succinimidyl ester, and isocyanate.

23. The adhesive hydrogel according to claim 20, wherein the nucleophilic groups of the first component are selected from the group consisting of primary amine, secondary amine, carboxyhydrazide, acetoacetate, and thiol.

24. The adhesive hydrogel according to claim 20, wherein the nucleophilic groups of the second component are selected from the group consisting of primary amine, secondary amine, carboxyhydrazide, acetoacetate, and thiol.

25. An adhesive hydrogel useful for applying a coating to an anatomical site on tissue of a living organism, the adhesive hydrogel obtained by a method comprising the steps of:
   a) applying to the site the first component of the anhydrous fibrous sheet of claim 1;
   b) applying to the site an aqueous solution or dispersion comprising the second component of the anhydrous fibrous sheet of claim 1; and
   c) allowing the first component and the second component to crosslink on the site, to form a hydrogel that is adhesive to the tissue.

26. An anhydrous fibrous sheet comprising
   a first component and a second component, wherein the first and second components are un-crosslinked and co-reactive with each other under physiological conditions,
   wherein the first component is a fibrous polymer and comprises at least one water-dispersible polyvinyl alcohol or polyvinyl alcohol copolymer having primary amine groups or secondary amine groups, and
   the second component is capable of crosslinking the first component when said sheet is exposed to an aqueous medium in contact with biological tissue to form a crosslinked hydrogel that is adhesive to the biological tissue;
   wherein the second component is a fibrous polymer having a backbone structure different from the fibrous polymer of the first component and comprises at least one water-dispersible linear or branched polyether derivatized with isocyanate groups; or
   the second component is a coating on the fibrous polymer of the first component and comprises at least one water-dispersible linear or branched polyether derivatized with isocyanate groups; or
   the second component is a dry powder dispersed and entrapped within interstices of the fibrous polymer of the first component and comprises at least one water-dispersible linear or branched polyether derivatized with isocyanate groups.

* * * * *